(12) United States Patent
Cardosi et al.

(10) Patent No.: US 8,815,076 B2
(45) Date of Patent: Aug. 26, 2014

(54) SYSTEMS AND METHODS FOR DETERMINING A SUBSTANTIALLY HEMATOCRIT INDEPENDENT ANALYTE CONCENTRATION

(71) Applicant: LifeScan Scotland Limited, Inverness-shire (GB)

(72) Inventors: Marco F. Cardosi, Croy (GB); Stephen Patrick Blythe, Inverness (GB); Matthew Finch, Nenagh (IE); Arlene Thompson, Inverness (GB); Nina Antonia Naylor, San Francisco, CA (US); Eric Jason Bailey, Oakland, CA (US); Michael Patrick Dolan, Mill Valley, CA (US); Gretchen Anderson, Oakland, CA (US); Lorraine Comstock, Saratoga, CA (US); Mary McEvoy, Belmont, CA (US); Thomas Sutton, Milan (IT); Richard Michael Day, Duncanston (GB); Leanne Mills, Milton of Leys (GB); Emma Vanessa Jayne Day, Culbokie Duncanston (GB); Christopher Philip Leach, Inverness (GB)

(73) Assignee: Lifescan Scotland Limited, Inverness (GB)

( * ) Notice: Subject to any disclaimer, the term of this patent is extended or adjusted under 35 U.S.C. 154(b) by 38 days.

(21) Appl. No.: 13/648,979

(22) Filed: Oct. 10, 2012

(65) Prior Publication Data
US 2013/0037421 A1 Feb. 14, 2013

Related U.S. Application Data

(60) Division of application No. 12/692,120, filed on Jan. 22, 2010, now Pat. No. 8,293,096, which is a continuation of application No. 12/305,360, filed as application No. PCT/GB2007/003791 on Oct. 5, 2007, now abandoned.

(60) Provisional application No. 60/850,211, filed on Oct. 5, 2006.

(51) Int. Cl.
*G01F 1/64* (2006.01)

(52) U.S. Cl.
USPC ............... 205/777.5; 204/43.01; 205/792

(58) Field of Classification Search
USPC ............... 204/403.01–403.15; 205/775, 792, 205/777.5
See application file for complete search history.

(56) References Cited

U.S. PATENT DOCUMENTS

| 5,187,100 A | 2/1993 | Matzinger et al. |
| 5,312,590 A | 5/1994 | Gunasingham |

(Continued)

FOREIGN PATENT DOCUMENTS

| AU | 2006200073 A1 | 2/2006 |
| EP | 0928967 A | 7/1999 |

(Continued)

OTHER PUBLICATIONS

L. Chen, et al., "*Bioinorganic Composites for Enzyme Electrodes*", Anal. Chem., vol. 73, No. 13, pp. 2862-2868, Jul. 1, 2001.

(Continued)

*Primary Examiner* — Luan Van
*Assistant Examiner* — Maris R Kessel

(57) ABSTRACT

A method and system is provided to allow for determination of substantially Hematocrit independent analyte concentration. In one example, an analyte measurement system is provided that includes a test strip and a test meter. The test strip includes a reference electrode and a working electrode, in which the working electrode is coated with a reagent layer. The test meter includes an electronic circuit and a signal processor. The electronic circuit applies a plurality of voltages to the reference electrode and the working electrode over respective durations. The signal processor is configured to determine a substantially hematocrit-independent concentration of the analyte from a plurality of current values as measured by the processor upon application of a plurality of test voltages to the reference and working electrodes over a plurality of durations interspersed with rest voltages lower than the test voltages being applied to the electrodes.

7 Claims, 13 Drawing Sheets

(56) References Cited

U.S. PATENT DOCUMENTS

| | | | |
|---|---|---|---|
| 5,605,837 | A | 2/1997 | Karimi et al. |
| 5,653,918 | A | 8/1997 | Towlson et al. |
| 5,708,247 | A | 1/1998 | McAleer et al. |
| 6,046,051 | A | 4/2000 | Jina |
| 6,179,979 | B1 | 1/2001 | Hodges et al. |
| 6,241,862 | B1 | 6/2001 | McAleer et al. |
| 6,448,794 | B1 | 9/2002 | Cheng et al. |
| 6,475,372 | B1 | 11/2002 | Ohara et al. |
| 7,112,265 | B1 | 9/2006 | McAleer |
| 2003/0116447 | A1 | 6/2003 | Surridge et al. |
| 2003/0143113 | A2 | 7/2003 | Yuzhakov et al. |
| 2003/0203498 | A1 | 10/2003 | Neel et al. |
| 2003/0217918 | A1 | 11/2003 | Davies et al. |
| 2004/0096959 | A1 | 5/2004 | Stiene et al. |
| 2004/0260511 | A1 | 12/2004 | Burke et al. |
| 2005/0096409 | A1 | 5/2005 | Davies et al. |
| 2008/0099347 | A1* | 5/2008 | Barlag et al. ............... 205/793.5 |

FOREIGN PATENT DOCUMENTS

| | | |
|---|---|---|
| EP | 1156324 A | 11/2001 |
| EP | 1264898 A2 | 12/2002 |
| EP | 1318399 A | 6/2003 |
| EP | 1426757 A | 6/2004 |
| EP | 1447660 A | 8/2004 |
| EP | 1452854 A1 | 9/2004 |
| EP | 1467206 A | 10/2004 |
| EP | 1496354 A | 1/2005 |
| EP | 1746413 A2 | 1/2007 |
| EP | 1775587 A | 4/2007 |
| EP | 1839571 A | 10/2007 |
| EP | 1840219 A | 10/2007 |
| WO | WO 01/67099 A1 | 9/2001 |
| WO | WO 01/73124 A3 | 10/2001 |
| WO | WO 02/49507 A1 | 6/2002 |
| WO | WO 03/097860 | 11/2003 |
| WO | WO 2004/039600 A2 | 5/2004 |
| WO | WO 2004/039897 A2 | 5/2004 |
| WO | WO 2004/040005 A1 | 5/2004 |
| WO | WO 2004/040285 A1 | 5/2004 |
| WO | WO 2004/040287 A1 | 5/2004 |
| WO | WO 2004/040290 A1 | 5/2004 |
| WO | WO 2004/040948 A1 | 5/2004 |
| WO | WO 2004/113910 A1 | 12/2004 |
| WO | WO 2005/045414 | 5/2005 |
| WO | WO 2005073708 A3 * | 10/2005 |
| WO | WO 2006/057722 | 6/2006 |
| WO | WO 2006/072089 | 7/2006 |

OTHER PUBLICATIONS

PCT Search Report, International Application No. PCT/GB2007/003791 dated Apr. 10, 2008, 5 pages.
PCT Search Report, International Application No. PCT/GB2007/003770 dated Jan. 16, 2008, 4 pages.
PCT Search Report, International Application No. PCT/GB2007/003790 dated Jan. 25, 2008, 4 pages.
PCT Search Report, International Application No. PCT/GB2007/003772 dated Jan. 21, 2008, 3 pages.
PCT Search Report, International Application No. PCT/GB2007/003781 dated Mar. 25, 2008, 3 pages.
European Search Report, European Patent Application No. 11190794.5 dated Mar. 7, 2012, 8 pages.

* cited by examiner

SYSTEMS AND METHODS FOR DETERMINING A SUBSTANTIALLY HEMATOCRIT INDEPENDENT ANALYTE CONCENTRATION

PRIORITY

This application is a divisional application of and claims the benefits of priority under 35 U.S.C. §119 and 120 to U.S. patent application Ser. No. 12/692,120, filed on Jan. 22, 2010; now allowed and which is a continuation of U.S. patent application Ser. No. 12/305,360, which is a National Stage application which claims priority from International Application Number PCT/GB2007/003791, filed Oct. 5, 2007, which claims priority from provisional application Ser. No. 60/850,211 filed on Oct. 5, 2006, in which all of the applications are incorporated by reference in their entirety herein.

DESCRIPTION OF THE RELATED ART

Electrochemical glucose test strips, such as those used in the OneTouch® Ultra® whole blood testing kit, which is available from LifeScan, Inc., are designed to measure the concentration of glucose in a blood sample from patients with diabetes. The measurement of glucose is based upon the specific oxidation of glucose by the flavo-enzyme glucose oxidase. The reactions that may occur in a glucose test strip are summarized below in Equations 1 and 2.

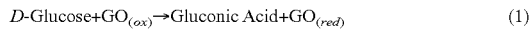
(1)

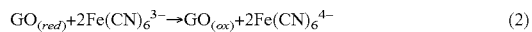
(2)

As shown in Equation 1, glucose is oxidized to gluconic acid by the oxidized form of glucose oxidase ($GO_{(ox)}$). It should be noted that $GO_{(ox)}$ may also be referred to as an "oxidized enzyme". During the reaction in Equation 1, the oxidized enzyme $GO_{(ox)}$ is converted to its reduced state which is denoted as $GO_{(red)}$ (i.e., "reduced enzyme"). Next, the reduced enzyme $GO_{(red)}$ is re-oxidized back to $GO_{(ox)}$ by reaction with $Fe(CN)_6^{3-}$ (referred to as either the oxidized mediator or ferricyanide) as shown in Equation 2. During the re-generation of $GO_{(red)}$ back to its oxidized state $GO_{(ox)}$, $Fe(CN)_6^{3-}$ is reduced to $Fe(CN)_6^{4-}$ (referred to as either reduced mediator or ferrocyanide).

When the reactions set forth above are conducted with a test voltage applied between two electrodes, a test current may be created by the electrochemical re-oxidation of the reduced mediator at the electrode surface. Thus, since, in an ideal environment, the amount of ferrocyanide created during the chemical reaction described above is directly proportional to the amount of glucose in the sample positioned between the electrodes, the test current generated would be proportional to the glucose content of the sample. A mediator, such as ferricyanide, is a compound that accepts electrons from an enzyme such as glucose oxidase and then donates the electrons to an electrode. As the concentration of glucose in the sample increases, the amount of reduced mediator formed also increases, hence, there is a direct relationship between the test current resulting from the re-oxidation of reduced mediator and glucose concentration. In particular, the transfer of electrons across the electrical interface results in a flow of test current (2 moles of electrons for every mole of glucose that is oxidized). The test current resulting from the introduction of glucose may, therefore, be referred to as a glucose current.

Because it can be very important to know the concentration of glucose in blood, particularly in people with diabetes, metering systems have been developed using the principals set forth above to enable the average person to sample and test their blood to determine the glucose concentration at any given time. The glucose current generated is monitored by the metering system and converted into a reading of glucose concentration using an algorithm that relates the test current to a glucose concentration via a simple mathematical formula. In general, the metering systems work in conjunction with a disposable test strip that includes a sample receiving chamber and at least two electrodes disposed within the sample-receiving chamber in addition to the enzyme (e.g. glucose oxidase) and the mediator (e.g. ferricyanide). In use, the user pricks their finger or other convenient site to induce bleeding and introduces a blood sample to the sample receiving chamber, thus starting the chemical reaction set forth above.

In electrochemical terms, the function of the meter is two fold. First, it provides a polarizing voltage (approximately 0.4 V in the case of OneTouch® Ultra®) that polarizes the electrical interface and allows current flow at the carbon working electrode surface. Second, it measures the current that flows in the external circuit between the anode (working electrode) and the cathode (reference electrode). The test meter may therefore be considered to be a simple electrochemical system that operates in a two-electrode mode although, in practice, a third and, even a fourth electrode may be used to facilitate the measurement of glucose and/or perform other functions in the test meter.

In most situations, the equation set forth above is considered to be a sufficient approximation of the chemical reaction taking place on the test strip and the test meter system outputting a sufficiently accurate representation of the glucose content of the blood sample. However, under certain circumstances and for certain purposes, it may be advantageous to improve the accuracy of the measurement. For example, blood samples having a high hematocrit level or low hematocrit level may cause a glucose measurement to be inaccurate.

A hematocrit level represents a percentage of the volume of a whole blood sample occupied by red blood cells. The hematocrit level may also be represented as a fraction of red blood cells present in a whole blood sample. In general, a high hematocrit blood sample is more viscous (up to about 10 centipoise at 70% hematocrit) than a low hematocrit blood sample (about 3 centipoise at 20% hematocrit). In addition, a high hematocrit blood sample has a higher oxygen content than low hematocrit blood because of the concomitant increase in hemoglobin, which is a carrier for oxygen. Thus, the hematocrit level can influence the viscosity and oxygen content of blood. As will be later described, both viscosity and oxygen content may change the magnitude of the glucose current and in turn cause the glucose concentration to be inaccurate.

A high viscosity sample (i.e., high hematocrit blood sample) can cause the test current to decrease for a variety of factors such as a decrease in 1) the dissolution rate of enzyme and/or mediator, 2) the enzyme reaction rate, and 3) the diffusion of a reduced mediator towards the working electrode. A decrease in current that is not based on a decrease in glucose concentration can potentially cause an inaccurate glucose concentration to be measured.

A slower dissolution rate of the reagent layer can slow down the enzymatic reaction as illustrated in Equations 1 and 2 because the oxidized enzyme $GO_{(ox)}$ must dissolve first before it can react with glucose. Similarly, ferricyanide ($Fe(CN)_6^{3-}$) must dissolve first before it can react with reduced enzyme $GO_{(red)}$. If the undissolved oxidized enzyme $GO_{(ox)}$ cannot oxidize glucose, then the reduced enzyme $GO_{(red)}$ cannot produce the reduced mediator $Fe(CN)_6^{4-}$ needed to generate the test current. Further, oxidized enzyme $GO_{(ox)}$ will react with glucose and oxidized mediator $Fe(CN)_6^{3-}$ more slowly if it is in a high viscosity sample as opposed to a low viscosity sample. The slower reaction rate with high viscosity samples is ascribed to an overall decrease in mass diffusion. Both oxidized enzyme $GO_{(ox)}$ and glucose must collide and interact together for the reaction to occur as shown in Equation 1. The ability of oxidized enzyme $GO_{(ox)}$ and glucose to collide and interact together is slowed down when they are in a viscous sample. Yet further, reduced mediator $Fe(CN)_6^{4-}$ will diffuse to the working electrode slower when dissolved in a high viscosity sample. Because the test current is typically limited by the diffusion of reduced mediator $Fe(CN)_6^{4-}$ to the working electrode, a high viscosity sample will also attenuate the test current. In summary, there are several factors that cause the test current to decrease when the sample has an increased viscosity.

A high oxygen content may also cause a decrease in the test current. The reduced enzyme $(GO_{(red)})$ can reduce oxygen $(O_2)$ to hydrogen peroxide as shown be Equation 3.

$$GO_{(red)} + O_2 \rightarrow GO_{(ox)} + H_2O_2 \qquad (3)$$

As noted earlier, the reduced enzyme $GO_{(red)}$ can also reduce ferricyanide $(Fe(CN)_6^{3-})$ to ferrocyanide $(Fe(CN)_6^{4-})$ as shown in Equation 2. Thus, oxygen can compete with ferricyanide for reacting with the reduced enzyme $(GO_{(red)})$. In other words, the occurrence of the reaction in Equation 3 will likely cause a decrease in the rate of the reaction in Equation 2. Because of such a competition between ferricyanide and oxygen, a higher oxygen content will cause less ferrocyanide to be produced. In turn, a decrease in ferrocyanide would cause a decrease in the magnitude of the test current. Therefore, a high oxygen content blood sample can potentially decrease the test current and affect the accuracy of the glucose measurement.

As such, there is great interest in the development of methods reducing the effects of hematocrit on a glucose measurement. In certain protocols, a pre-cast blood filtering membrane that is separate from the reagent layer has been employed to remove red blood cells and thereby reduce the hematocrit effect. The pre-cast blood filtering membrane that is separated from the reagent layer can be deposed on the working electrode. The use of a discrete pre-cast blood filtering membrane is unsatisfactory in that it requires a more complex test strip, increased sample volume, and increased testing time. The blood filtering membrane retains a certain amount of blood that does not contact the working electrodes causing a need for a larger blood sample. In addition, a finite amount of time is needed for the blood to be filtered by the membrane causing an increase in the overall test times. Applicants recognize that it would be advantageous to reduce the effects of hematocrit without using a pre-cast blood filtering membrane that is separate from the reagent layer.

Applicants also recognize that it would be advantageous to implement a system that does not use a pre-cast membrane to reduce the effects of hematocrit but instead uses multiple test voltages in which the magnitude of the voltage is pulsed between at least two or more values. More particularly, applicants realize that it would be advantageous to develop an algorithm that mathematically processes the collected test current values using multiple test voltages such that a substantially hematocrit independent glucose concentration can be determined.

SUMMARY OF THE INVENTION

In one aspect, a method of determining a substantially hematocrit-independent concentration of an analyte in a fluid sample deposited on a test strip. The test strip having a reference electrode and a working electrode, in which the working electrode is coated with a reagent layer. The method can be achieved by: applying a fluid sample to the test strip for a reaction period; applying a first test voltage to the reference electrode and the working electrode and measuring a first current value therebetween, the first test voltage being an absolute value from about 100 millivolts to about 600 millivolts; applying a first rest voltage between the reference electrode and the working electrode, the first rest voltage is an absolute value from about zero to about 50 millivolts; applying a second test voltage between the reference electrode and the working electrode and measuring a second current value, in which the second test voltage is an absolute value from about 100 millivolts to about 600 millivolts; applying a second rest voltage between the reference electrode and the working electrode, in which the second rest voltage is an absolute value from about zero to about 50 millivolts; applying a third test voltage between the reference electrode and the working electrode and measuring a third current value, in which the third test voltage is an absolute value from about 100 millivolts to about 600 millivolts; and calculating substantially hematocrit-independent concentration of the analyte from the first, second and third current values.

In another aspect, a method of detecting the presence of sufficient quantity of a fluid sample deposited on a test strip is provided. The test strip has a reference electrode and a working electrode, in which the working electrode is coated with a reagent layer. The method can be achieved by: applying a forward test voltage between the reference electrode and the working electrode and measuring a forward current value near the end of the forward test voltage, in which the forward test voltage is from about 100 millivolts to about 600 millivolts; applying a reverse test voltage of opposite polarity and substantially equal magnitude to the forward test voltage and measuring a reverse current value near the end of the reverse test voltage, the reverse test voltage being from about negative 100 millivolts to about negative 600 millivolts; calculating a ratio of the reverse current value to the forward current value; and determining if the ratio of the reverse current value to the forward current value is within an acceptance range, the acceptance range being substantially equal to two when the reference electrode is about twice the surface area of the working electrode.

In yet another aspect, a method of checking a functionality of a test strip is provided. The test strip has a reference electrode and a working electrode with the working electrode being coated with a reagent layer. The method can be achieved by: applying a fluid sample to the test strip for a reaction period; applying a first test voltage between the reference electrode and the working electrode and measuring a first current value, in which the first test voltage is an absolute value from about 100 millivolts to about 600 millivolts; applying a first rest voltage between the reference electrode and the working electrode, the first rest voltage is an absolute value from about zero to about 50 millivolts; applying a second test voltage between the reference electrode and the working electrode and measuring a second current value, in which the second test voltage is an absolute value from about 100 millivolts to about 600 millivolts; applying a second rest voltage between the reference electrode and the working electrode, in which the second rest voltage is an absolute value from about zero to about 50 millivolts; applying a third test voltage between the reference electrode and the working electrode and measuring a third current value, in which the third test voltage is an absolute value from about 100 millivolts to about 600 millivolts; applying a third rest voltage between the reference electrode and the working electrode, in which the third rest voltage is an absolute value from about zero to about 50 millivolts; applying a fourth test voltage between the reference electrode and the working electrode and measuring a fourth current value, in which the fourth test voltage is an absolute value from about 100 millivolts to about 600 millivolts; applying a fourth rest voltage between the reference electrode and the working electrode, in which the fourth rest voltage is an absolute value from about zero to about 50 millivolts; applying a fifth test voltage between the reference electrode and the working electrode and measuring a fifth current value, in which the fifth test voltage is an absolute value from about 100 millivolts to about 600 millivolts; generating a curve representing the first, second, third, fourth and fifth current values as a function of pulse time, in which the pulse time is measured relative to initiation of the first test voltage; using least squares regression to fit the curve to the following equation:

$$I_i = \hat{\alpha}\sqrt{\frac{t_1}{t_i}} + \hat{\beta}\left(1 - \frac{t_1}{t_i}\right) + \eta_i$$

where:
$I_i$ is the current value measured at the end of each test voltage obtained at pulse time $t_i$ in which i varies from 1 to 5;
$\eta_i$ is a noise term;
$\hat{\alpha}$ is first shape parameter defined by the following equation:

$$\hat{\alpha} = \sum_{i=1}^{n} \lambda_i I_i;$$

where:

$$\lambda_i = \frac{S_{XX}Y_i - S_{XY}X_i}{\Delta};$$

$$X_i = 1 - \frac{t_i}{t_1};$$

$$Y_i = \sqrt{\frac{t_1}{t_i}};$$

$$S_{AB} = \sum_{i=1}^{n} A_i B_i;$$

$$\Delta = S_{XX}S_{YY} - S_{XY}^2;$$

and
$\hat{\beta}$ is second shape parameter defined by the following equation:

$$\hat{\beta} = \sum_{i=1}^{n} \theta_i I_i;$$

where $\theta_i = \frac{S_{YY}X_i - S_{XY}Y_i}{\Delta}$.

calculating a $\lambda$ and $\theta$ value for each pulse time and storing the $\lambda$ and $\theta$ values in a look up table in the metering system; calculating a $\hat{\alpha}$ value and a $\hat{\beta}$ value using the five current values and the $\lambda$ and $\theta$ values from the look up table to obtain a best fit to the curve; and calculating a ratio of a to $\hat{\alpha}$ to $\hat{\beta}$ for the test strip and comparing the ratio of $\hat{\alpha}$ to $\hat{\beta}$ to an acceptance range for a test strip which is functioning normally.

In a further aspect, an analyte measurement system is provided that includes a test strip and a test meter. The test strip includes a reference electrode and a working electrode, in which the working electrode is coated with a reagent layer. The test meter includes an electronic circuit and a signal processor. The electronic circuit applies a plurality of voltages to the reference electrode and the working electrode over respective durations. The signal processor is configured to determine a substantially hematocrit-independent concentration of the analyte from a plurality of current values as measured by the processor upon application of a plurality of test voltages to the reference and working electrodes over a plurality of durations interspersed with rest voltages lower than the test voltages being applied to the electrodes.

BRIEF DESCRIPTION OF THE DRAWINGS

A better understanding of the features and advantages will be obtained by reference to the following detailed description that sets forth illustrative embodiments, in which the principles of the invention are utilized, and the accompanying drawings, of which.

Figure 23:
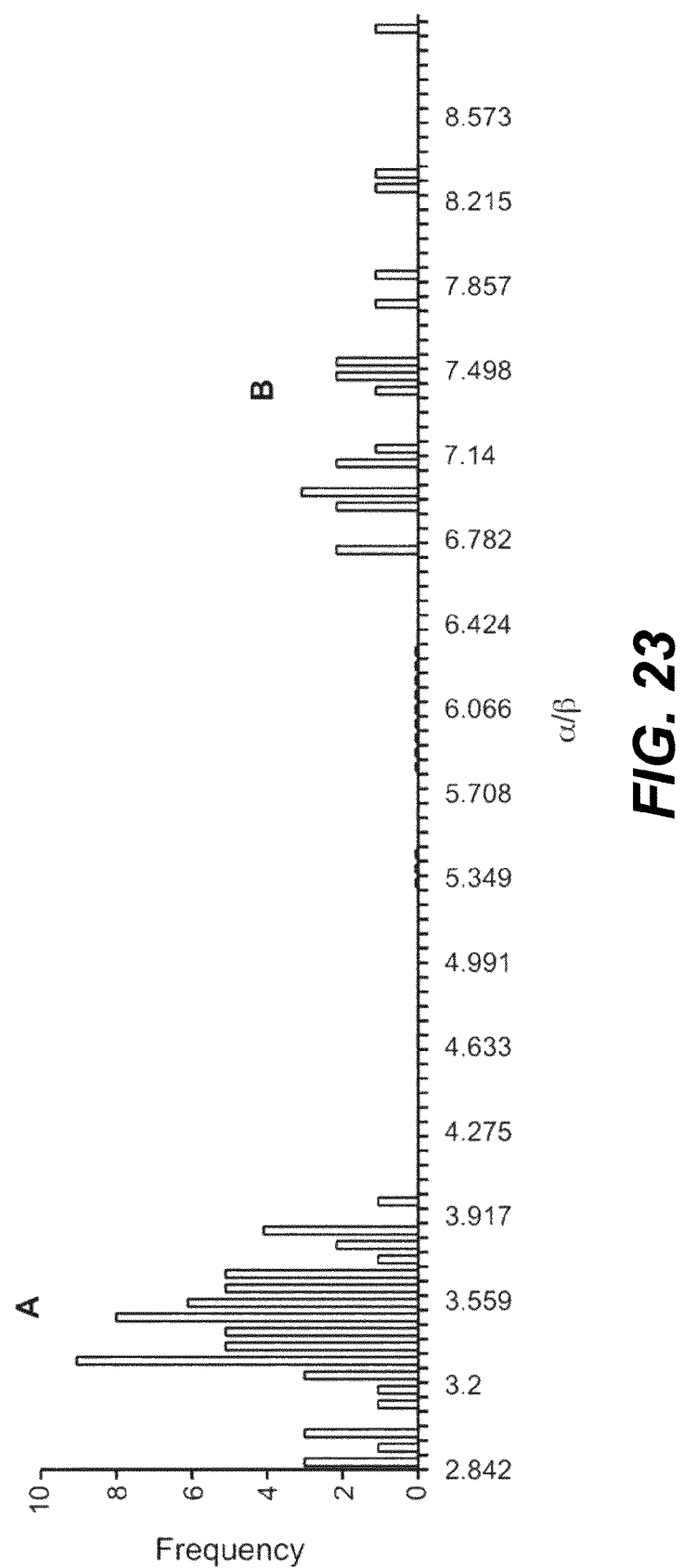
Figure 24:
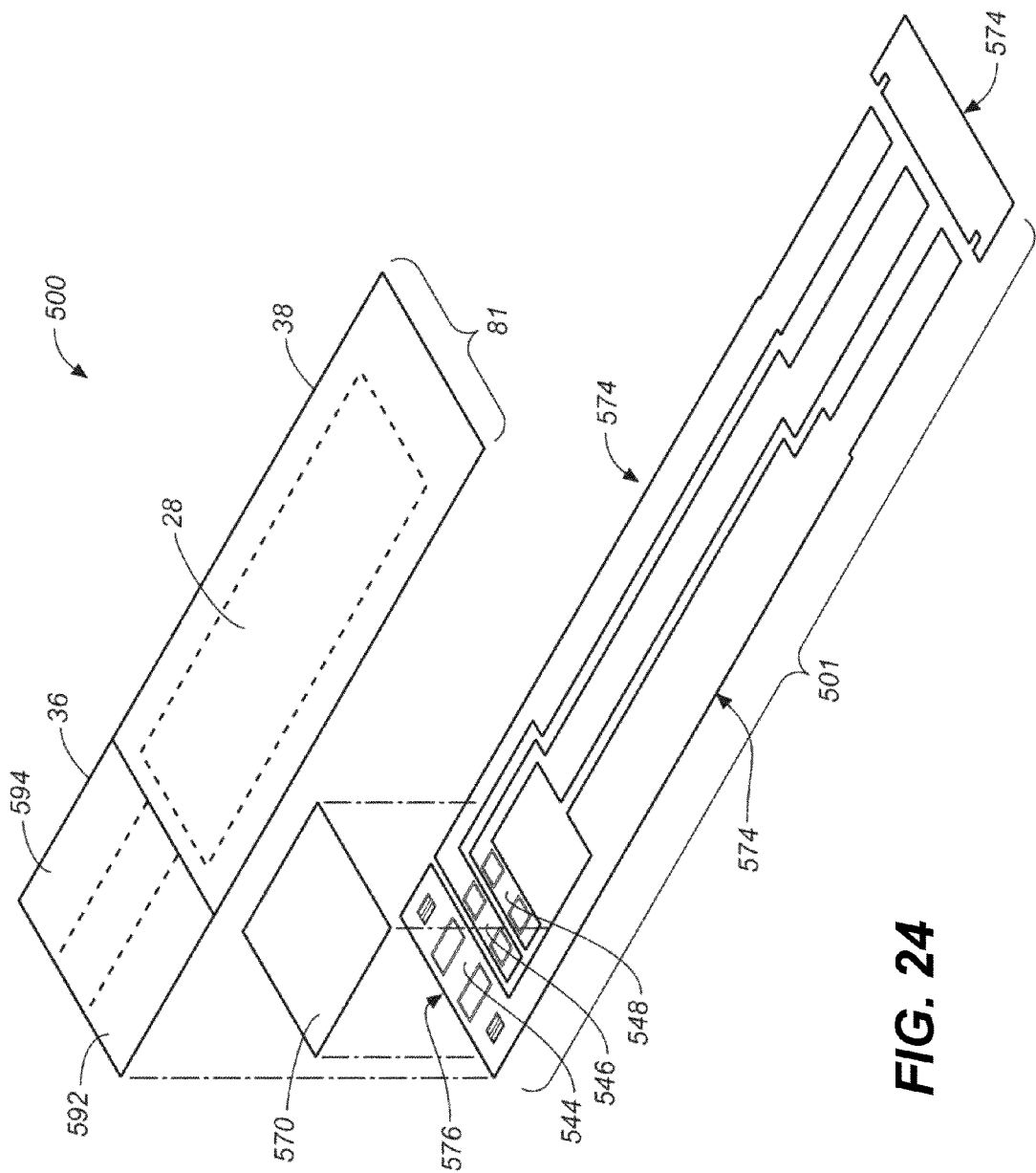
Figure 25:
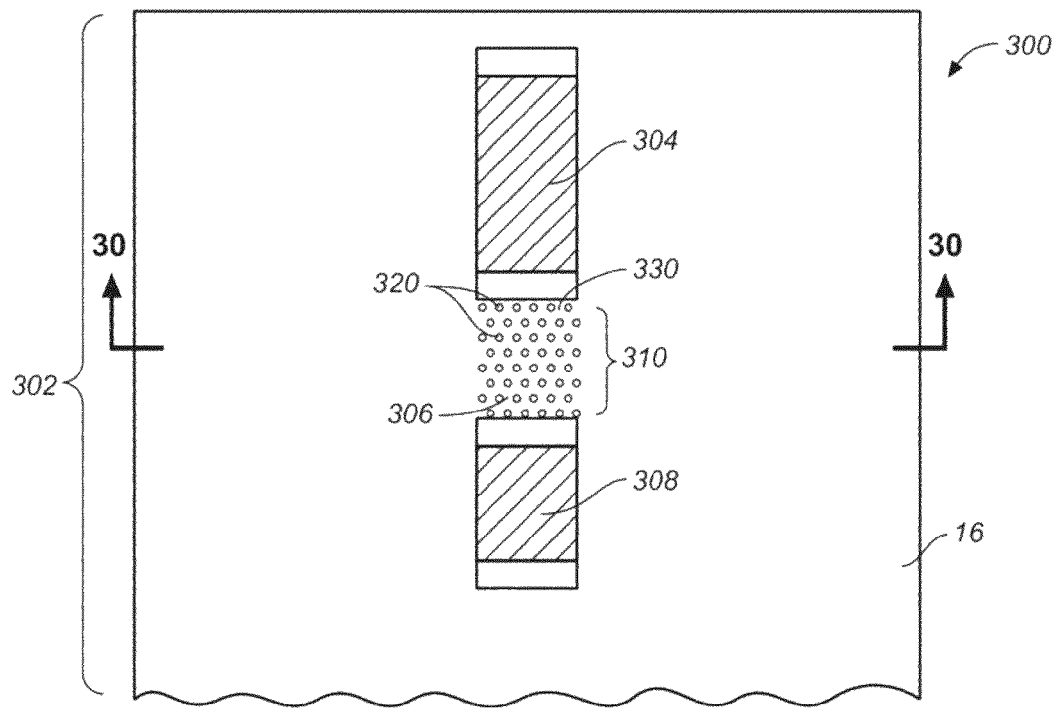
Figure 26:
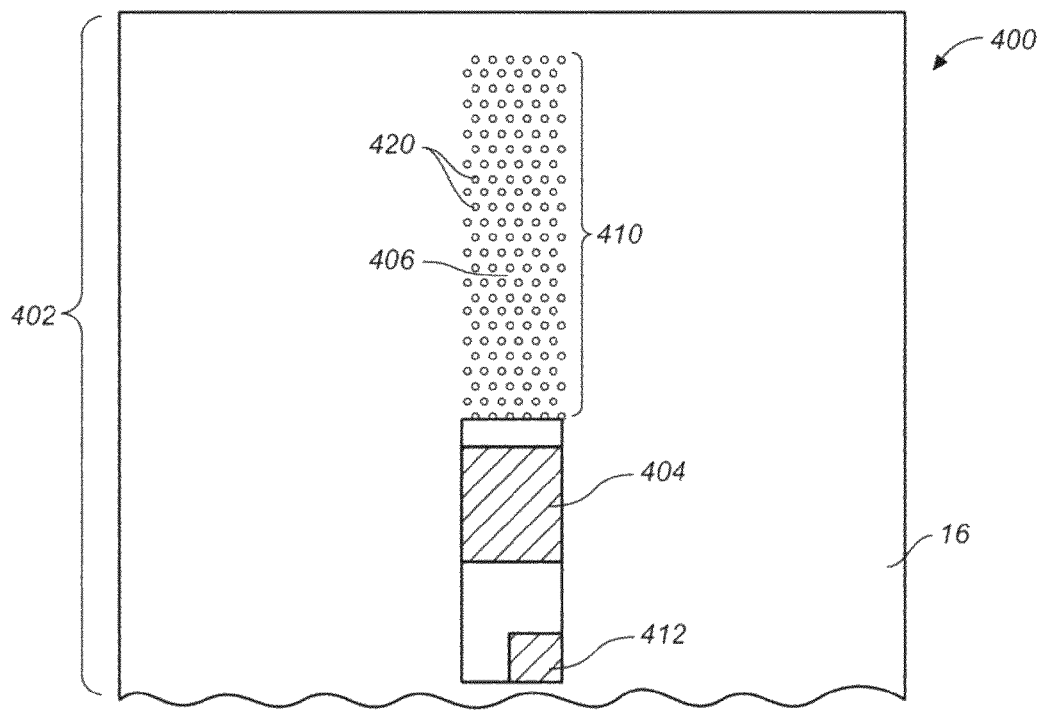
Figure 27:
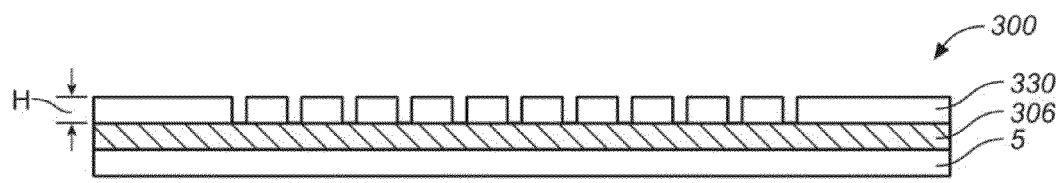
Figure 28:
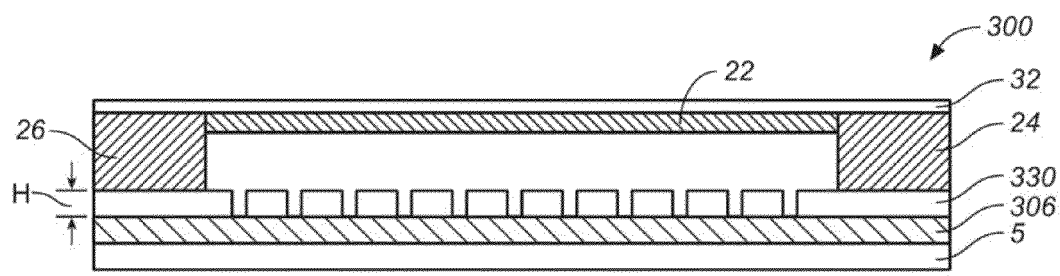
Figure 29:
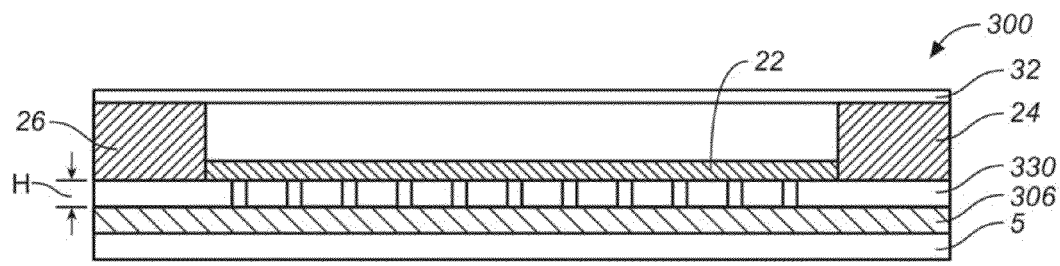
Figure 30:
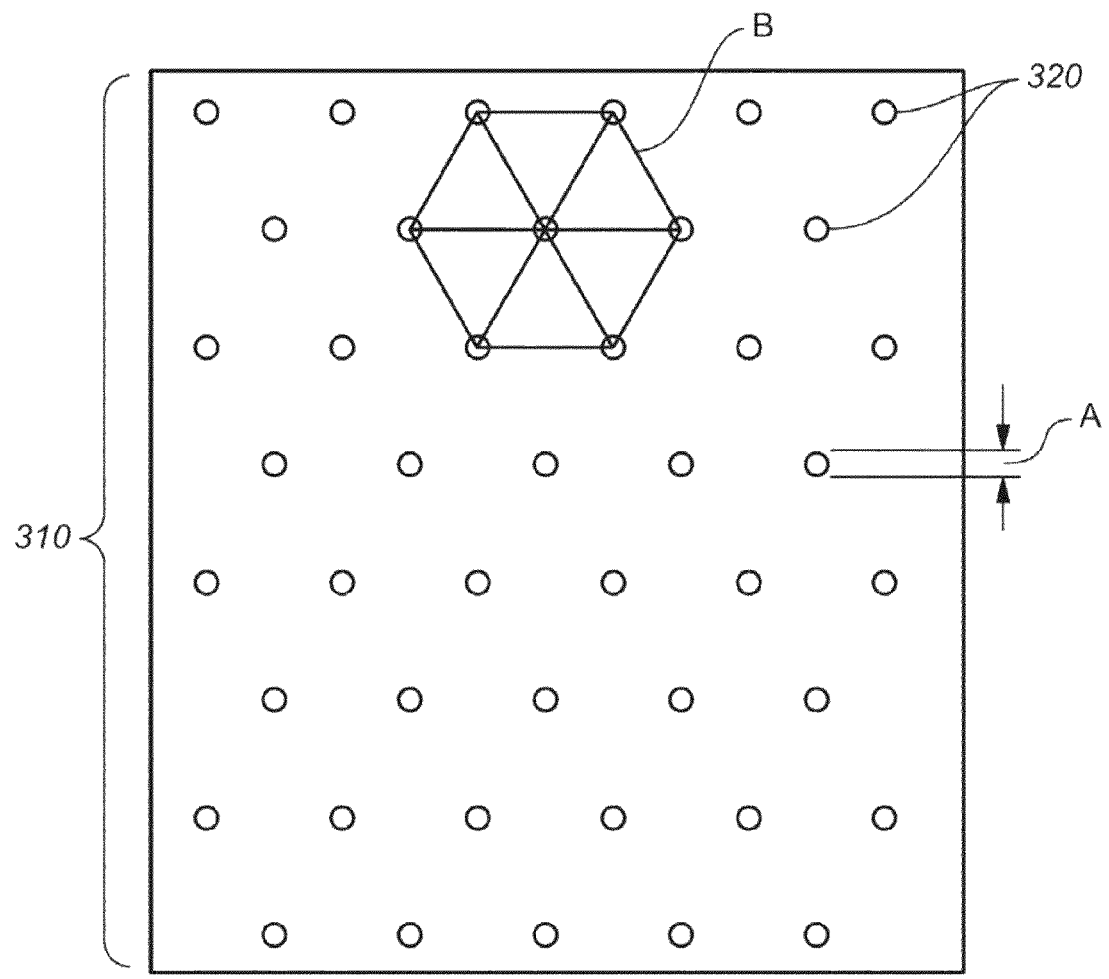

ratios for test strips exhibiting normal and abnormal responses according to a method;

FIG. 23 is a graph showing frequency as a function of $$\frac{\hat{\alpha}}{\hat{\beta}}$$

ratio for non-aged (i.e. group B) and aged (i.e., group A) test strips according to a method;

FIG. 24 illustrates a top exploded perspective view of an unassembled test strip which is an embodiment;

FIGS. 25 and 26 are top views of a distal portion of a partially assembled test strip that is suitable for use with the present invention;

FIG. 27 is a cross sectional view of the test strip shown in FIG. 26 through a microelectrode array on a first working electrode;

FIG. 28 is a cross sectional view through a microelectrode array on a first working electrode 306 of FIG. 25 with additional layers coated on an insulation portion including a reagent layer, adhesive pads, and a hydrophilic portion. The reagent layer is disposed on the distal side of the hydrophilic portion;

FIG. 29 is a cross sectional view through a microelectrode array on a first working electrode 306 of FIG. 25 with additional layers coated on an insulation portion including a reagent layer, adhesive pads, and a hydrophilic portion. The reagent layer is disposed over the insulation portion; and FIG. 30 is a top, close up view of the microelectrode array on the first working electrode of the test strip shown in FIG. 25.

DETAILED DESCRIPTION OF THE INVENTION

The invention disclosed herein relates to systems and methods for measuring the concentration of an analyte in a fluid sample. The disclosure below emphasizes the measurement of a glucose concentration in a whole blood sample; however, the person of ordinary skill will recognize that the description is readily adapted to measure the properties of other analytes, such as cholesterol, ketone bodies or alcohol, and to other fluids such as saliva, urine, interstitial fluid, or test strip control solutions.

It will be further understood that this invention is not limited to only correcting for hematocrit and can also be applicable to correcting for the effects of variable viscosity or oxygen content in samples. For example, blood can have a high viscosity for a variety of other reasons in addition to high hematocrit. For example, a low temperature (e.g., around 10° C.), high lipid concentration, and/or high protein concentration can also cause a blood sample to become more viscous.

Figure 1:
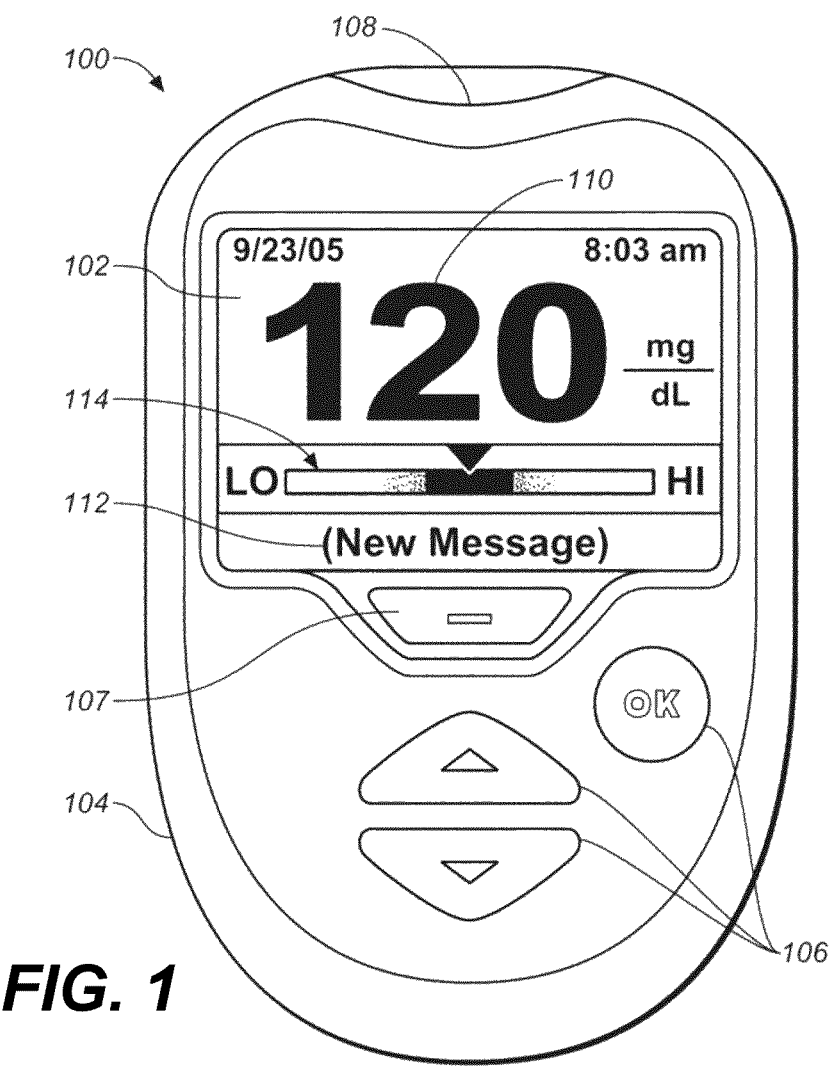
FIG. 1 is a top view of a metering system incorporating an algorithm according to exemplary embodiments.

It will yet further be understood that, the invention would also be applicable for reducing the effects caused by oxygen and/or viscosity of physiological fluids other than blood. For example, physiological fluids may also include plasma, serum, interstitial fluid, and a combination thereof. It should be noted that it is not uncommon for extracted interstitial fluid samples to be partially mixed with blood.
in which FIG. 1 illustrates a metering system 100 suitable for connecting to test strip 90. Metering system 100 includes a display 102, a housing 104, a plurality of user interface buttons 106, an optional soft key 107 and a strip port connector 108. Metering system 100 further includes electronic circuitry within housing 104 such as a memory 190, a microprocessor 192, electronic components for applying a test voltage, and also for measuring a plurality of test current values (see 190 and 192 in FIG. 6). Proximal portion 4 of test strip 90 may be inserted into strip port connector 108. Display 102 may output an analyte concentration 110 and may be used to show a user interface for prompting a user on how to perform a test. A plurality of user interface buttons 106 and optional soft key 107 allow a user to operate metering system 100 by navigating through the user interface software. Unlike user interface buttons 106 that only possess one function, soft key 107 may perform multiple functions, depending on the menu displayed on display 102. For example, soft key 107 may perform at least one of the following functions: back, more, add information, edit information, add comment, new message and exit. Soft key 107 may be located in any location convenient for the user of metering system 100. In one embodiment, soft key 107 is located directly underneath and in close proximity to a function text 112 on display 102 as shown in FIG. 1.

Figure 2:
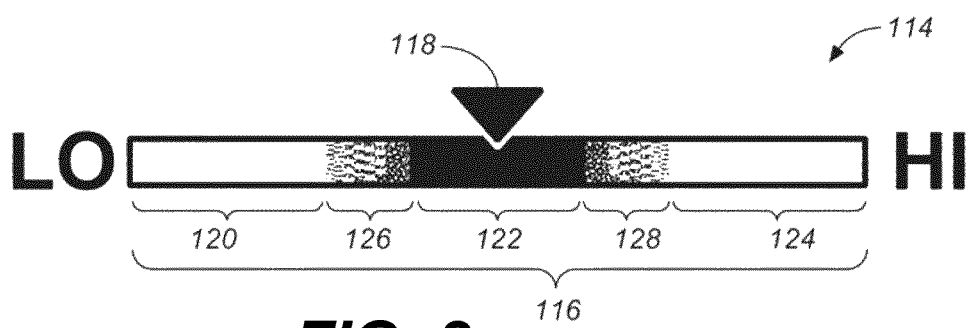
FIG. 2 is a top, close up view of the range indicator on the display of the metering system shown in FIG. 1 according to an exemplary embodiment.

Referring to FIGS. 1 and 2, display 102 further includes a range indicator 114 for representing an analyte concentration 110. Range indicator 114 is optionally located below analyte concentration 110. Range indicator 114 includes a plurality of ranges 116 for indicating whether analyte concentration 110 is within a normal range 122 and a graphical element 118 for marking a region of range indicator 114 on which analyte concentration 110 falls. The plurality of ranges 116 includes a low range 120, a normal range 122 and a high range 124. Text labeling low, normal and high ranges is optionally located in close proximity to range indicator 114 such that graphical element 118 in not hindered. For example, text may be located below, above or to the left and/or right side of range indicator 114. Numerical values for the lower and upper limits of normal range 122 may also optionally be located above, below or to the left and/or right side of range indicator 114. In one exemplary embodiment in which analyte concentration 110 is a glucose concentration, the lower and upper limits of normal range 122 are optionally configurable by the user (e.g., the patient or health care provider) of the metering system and may be tailored to whether a measurement is taken pre-meal or post-meal. For example, the lower and upper limits of normal range 122 may be set at 70 mg/dL and 110 mg/dL, respectively, for a pre-meal measurement or the lower and upper limits may be set at 90 mg/dL and 140 mg/dL, respectively, for a post-meal measurement. In another embodiment, the lower and upper limits are set at 70 mg/dL and 140 mg/dL, respectively, to encompass any glucose concentration within normal range 122 regardless of whether a measurement is taken pre- or post meal. Plurality of ranges 116 is represented as a continuum in which the range indicators are distinguished from each other by color or by gradual changes in shade. In the embodiment shown in FIGS. 1 and 2, a first transition region 126 between low range 120 and normal range 122 and a second transition region 128 between normal range 122 and high range 124 is illustrated as a gradual change in color or a gray region to indicate that the boundaries between the low, normal and high ranges are not well defined and are therefore cautionary regions. Graphical element 118 may be an arrow or may be triangular in shape and may be located above, below and/or slightly overlapping with range indicator 114. The orientation of graphical element 118 is such that it points from the general direction of analyte concentration 110 displayed on metering system 100 to the region of range indicator 114 on which analyte concentration 110 falls, giving contextual information to the user of metering system 100. Analyte concentration 110 is generally located in the upper half of display 102. The size of analyte concentration 110 displayed on metering system 100 is such that it is easy to read for users who have limited eyesight. In one embodiment, the font size of analyte concentration 110 is at least 72. In another embodiment, analyte concentration 110 occupies at least 25% of the display area. Display 102 may also optionally show the test date and test time.

Figure 3:
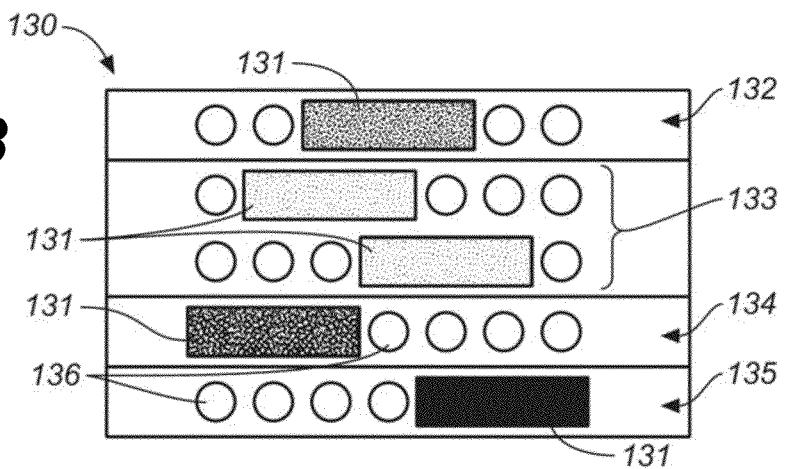
FIG. 3 is top, close up of a range indicator according to another exemplary embodiment.

FIG. 3 illustrates another exemplary embodiment of a range indicator 130 according to the present invention. Range indicator 130 includes a sliding bar 131 for indicating if a measured analyte concentration is within a normal range 132, within a borderline range 133, within a low range 134 or within a high range 135. Borderline range 133 is located between low range 134 and normal range 132 or between normal range 132 and high range 135. Sliding bar 131 may move along range indicator 130 and may change color, depending on where sliding bar 131 is located on range indicator 130. In one embodiment, when the measured analyte concentration is within normal range 132, sliding bar 131 is green in color and is located approximately at the center of range indicator 130. When the measured analyte concentration is within borderline range 133, sliding bar 131 may be yellow or orange in color and is located slightly to the left or right of the center of range indicator 130. Sliding bar 131 having a blue color represents low range 134 and is located to the far left of range indicator 130. When sliding bar 131 is red in color and is located to the far right of range indicator 130, high range 135 is represented. Other colors may also be used for sliding bar 131 to represent normal, borderline, low and high ranges 132, 133, 134, 135. Range indicator 130 may optionally include a plurality of geometric symbols 136 (e.g., open or solid and/or colored circles, squares, triangles, and/or rectangles) to represent regions on range indicator 130 that do not include sliding bar 131. Text or characters (e.g., Kanji characters) to denote when a measured analyte concentration is within low range 134 or within high range 135 may optionally be located in close proximity to range indicator 130. For example, text and/or characters may be located below, above or to the left and/or right side of range indicator 130. In one exemplary embodiment in which the measured analyte concentration is a glucose concentration, the lower and upper limits of normal range 122 are optionally configurable by the user (e.g., the patient or health care provider) of the metering system. For example, the lower and upper limits of normal range 122 may be set at 70 mg/dL and 140 mg/dL, respectively, to encompass any glucose concentration within normal range 132 regardless of when the measurement is taken. Range indicator 130 is generally located in the bottom portion of the metering system display below the displayed analyte concentration.

Figure 4:
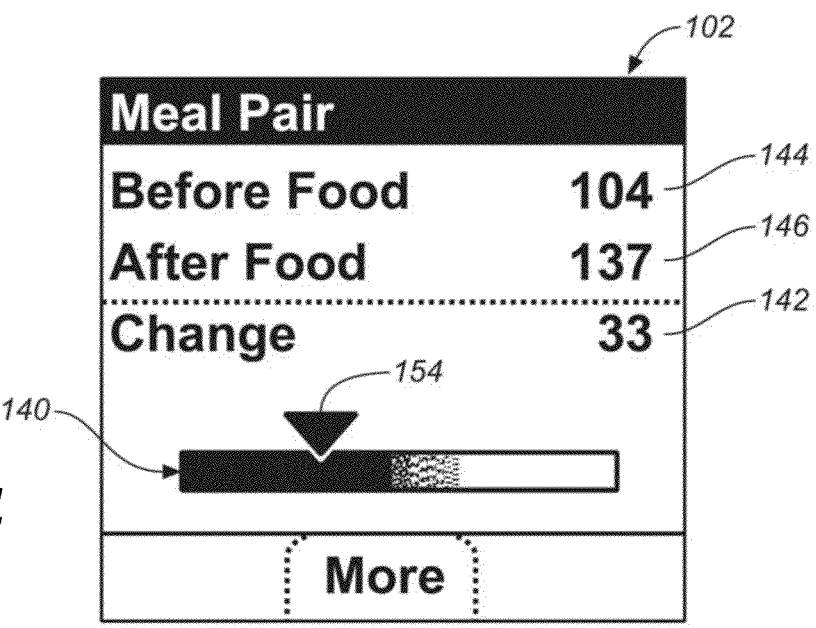
FIG. 4 is an alternative view of a metering system display with a range indicator according to an exemplary embodiment.
Figure 5:
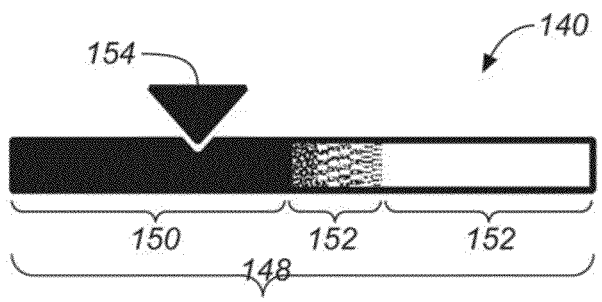
FIG. 5 is a top, close up view of the range indicator on the display shown in FIG. 4.

In another embodiment shown in FIGS. 4 and 5, a range indicator 140 represents a change in analyte concentration 142 between a before food value 144 and an after food value 146. Range indicator 140 includes a plurality of ranges 148 for indicating whether change in analyte concentration 142 is within an acceptable change range 150 or an unacceptable change range 152. Range indicator 140 also includes a graphical element 154 for marking a region of range indicator 140 on which change in analyte concentration 142 falls. Text labeling the change ranges may optionally be located in close proximity to range indicator such that graphical element 154 is not hindered. For example, text may be located below, above or to the left and/or right side of range indicator 114. A numerical value for the upper limit of acceptable change range 150 may also optionally be located above or below range indicator 114. The upper limit of acceptable change range 150 is configurable by the user (e.g., the patient or health care provider) and generally ranges from about 20 to about 70, more usually about 50. Plurality of ranges 148 is represented as a continuum in which the ranges are distinguished from each other by color or by gradual changes in shade. In the embodiment shown in FIGS. 4 and 5, a transition region 156 between acceptable change range 150 and unacceptable change range 152 is by a gradual change in color or a gray region to indicate that the boundaries between the change ranges are not well defined and are therefore cautionary regions. Graphical element 154 may be an arrow or may be triangular in shape and may be located above, below and/or slightly overlapping with range indicator 140. The orientation of graphical element 154 is such that it points from the general direction of change in analyte concentration 142 displayed on metering system 100 to the region of range indicator 140 on which change in analyte concentration 142 falls.

Figure 6:
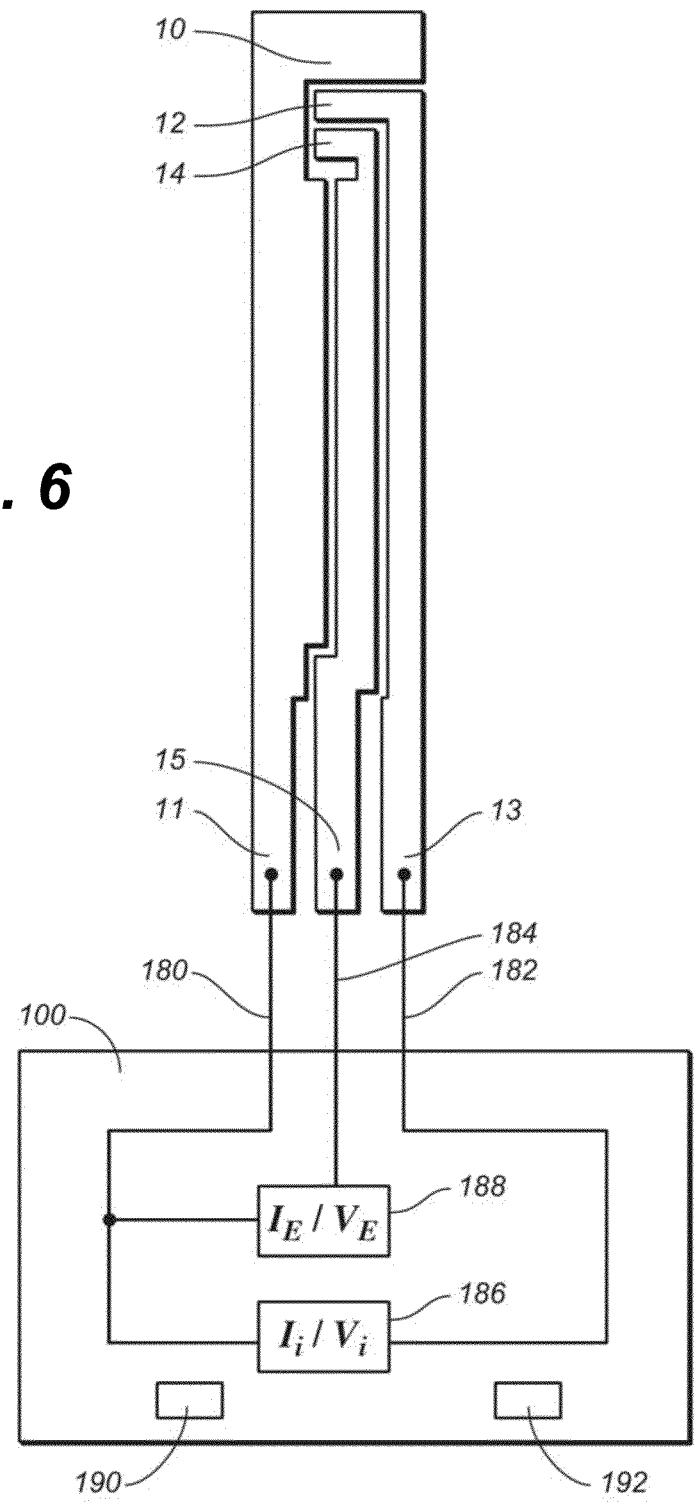
FIG. 6 is a simplified schematic view of the metering system of FIG. 1 forming an electrical connection with a test strip.

FIG. 6 shows a simplified schematic of a metering system 100 interfacing with test strip 90. Metering system 100 includes a reference connector 180, a first connector 182 and a second connector 184, respectively, which form an electrical connection to reference contact 11, first contact 13 and second contact 15. The three aforementioned connectors are part of strip port connector 108. When performing a test, a first test voltage source 186 may apply a plurality of test voltages $V_i$ between first working electrode 12 and reference electrode 10, in which i ranges from 1 to n and more typically 1 to 5. As a result of the plurality of test voltages $V_i$, metering system 100 may then measure a plurality of test currents $I_i$. In a similar manner, second test voltage source 188 may apply a test voltage $V_E$ between second working electrode 14 and reference electrode 10. As a result of the test voltage $V_E$, metering system 100 may then measure a test current $I_E$. Test voltages $V_i$ and $V_E$ may be applied to first and second working electrodes, respectively, either sequentially or simultaneously. Those skilled in the art will recognize that the working electrode to which $V_i$ and $V_E$ are applied may be switched, i.e., that $V_i$ may be applied to second working electrode and $V_E$ may be applied to first working electrode.

In general, it is desirable to use a test voltage which is more positive than a redox voltage of the mediator used in the test strip. In particular, the test voltage should exceed the redox voltage by an amount sufficient to ensure that the resulting test current will not be dependent on small variations in the test voltage. Note that a redox voltage describes a mediator's intrinsic affinity to accept or donate electrons when sufficiently close to an electrode having a nominal voltage. When a test voltage is sufficiently positive with respect to the mediator's redox voltage, the mediator will be rapidly oxidized. In fact, the mediator will be oxidized so quickly at a sufficiently positive test voltage (i.e., limiting test voltage) that the test current magnitude will be limited by the diffusion of the mediator to the electrode surface (i.e., limiting test current). For an embodiment where first working electrode 12 is a carbon ink and the mediator is ferricyanide, a test voltage of about +400 millivolts may be sufficient to act as a limiting test voltage. For an embodiment where first working electrode 12 is a carbon ink and the mediator is $Ru^{III}(NH_3)_6$, a test voltage of about +200 millivolts may be sufficient to act as a limiting test voltage. It will be apparent to one skilled in the art that other mediator and electrode material combinations will require different limiting test voltages.

Methods that use the aforementioned test strip 90 and metering system 100 embodiments will now be described.

In step (a) of a method for determining a substantially hematocrit independent analyte (e.g., glucose) concentration, metering system 100 and a test strip 90 are provided according to exemplary embodiments. Metering system 100 includes electronic circuitry that can be used to apply a plurality of test voltages to the test strip and to measure current flowing through the first working electrode. Metering system 100 also includes a signal processor with an algorithm for the method of calculating an analyte concentration (e.g., glucose concentration) in a fluid sample as disclosed herein. In one embodiment the analyte is blood glucose and the fluid sample is whole blood, or a derivative or a fraction thereof.

Figure 7:
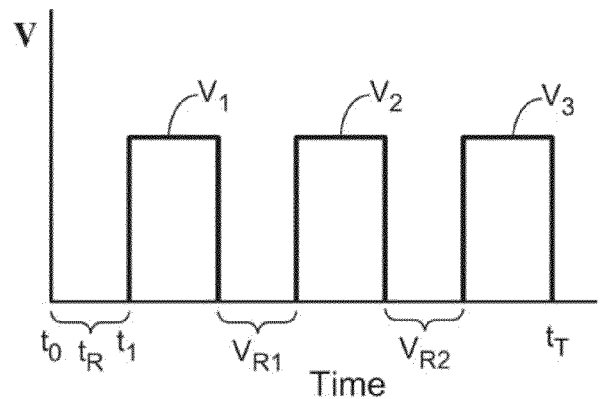
FIG. 7 is a graphical representation of a plurality of test voltages applied to a first working electrode of a test strip according to a method.

FIG. 7 is a graphical representation of a plurality of test voltages $V_i$ applied to test strip 90 in accordance with the method, where i ranges from 1 to 3 or more. Before the fluid sample is applied to test strip 90, metering system 100 is in a fluid detection mode in which a test voltage (not shown) of about 400 millivolts is applied between first working electrode 12 and reference electrode 10. In step (b) of the subject method the fluid sample is applied to test strip 90 at $t_0$ and is allowed to react with reagent layer 22 for a reaction period $t_R$. The presence of sufficient quantity in the reaction zone of test strip 90 is determined by measuring the current flowing through first working electrode 12. The beginning of reaction period $t_R$ is determined to begin when the current flowing through first working electrode 12 reaches a desired value, typically about 0.150 nanoamperes (not shown), at which point a voltage of about −50 millivolts to about +50 millivolts, typically zero millivolts, is applied between first working electrode 12 and reference electrode 10. Reaction period $t_R$ is typically from about 0 seconds to about 5 seconds and is more typically about 2.5 seconds or less. After reaction period $t_R$, the plurality of test voltages $V_i$ in the subject method are applied to test strip 90 for a total test time $t_T$ as shown in FIG. 7. The constituents of the fluid sample may vary, but in many embodiments the fluid sample is generally whole blood or a derivative or fraction thereof. The amount of fluid sample that is applied to test strip varies, but is generally from about 0.1 to about 10 microliters (μL), typically from about 0.9 to 1.6 μL. The sample is applied to test strip using any convenient protocol, such as injection or wicking, as may be convenient. The person of ordinary skill in the art will recognize that, if test strip is a dry phase reagent strip, sufficient quantity should be provided to complete an electrical circuit between the first working electrode and the reference electrode.

Figure 8:
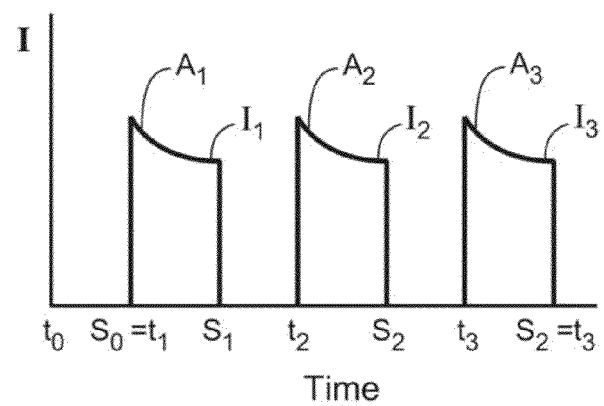
FIG. 8 is a graphical representation of the current transients obtained when the plurality of test voltages of FIG. 7 are applied to a test strip according to a method.
Figure 9:
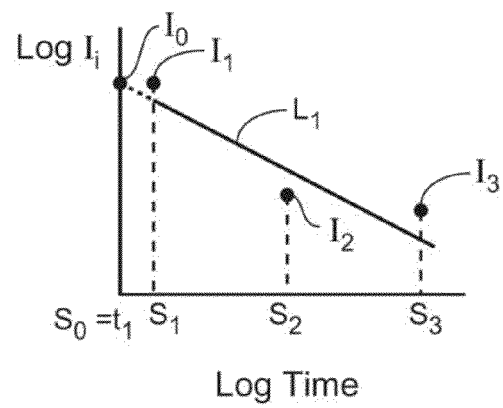
FIG. 9 is a logarithmic graph of the current values obtained from the current transients shown in FIG. 8 plotted as a function of the time at which the current values are measured according to a method.
Figure 10:
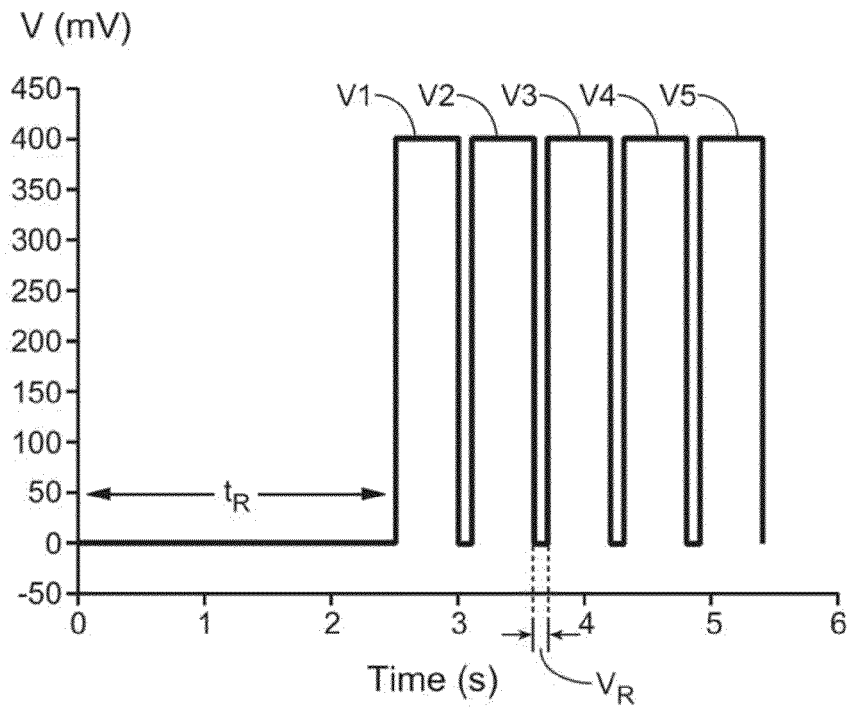
FIG. 10 is a graphical representation of five test voltages applied to a test strip according to a method.

FIG. 8 is a graphical representation of current transients $A_i$ (i.e., the measured electrical current response in nanoamperes as a function of time) that are measured when the plurality of test voltages $V_i$ of FIG. 8 are applied to test strip 90, where i ranges from 1 to 3 or more. Current values $I_i$ obtained from current transients $A_i$ are generally indicative of the analyte concentration in the sample as will be described with reference to Example 1 below. Referring to FIGS. 9 and 10, in step (c) of the subject method, a first test voltage $V_1$ is applied between first working electrode 12 and reference electrode 10 at time $t_1$ and a first current value $I_1$ is measured at or near the end of first test voltage $V_1$ at time $S_1$. First test voltage $V_1$ applied between first working electrode 12 and reference electrode 10 is generally from about +100 millivolts to about +600 millivolts or from about negative 100 millivolts to about negative 600 millivolts. In one embodiment in which first working electrode 12 is a carbon ink and the mediator is ferricyanide, a test voltage of about +400 millivolts is used. In another embodiment in which first working electrode 12 is a carbon ink and the mediator is ruthenium hexamine trichloride, a test voltage of about +200 millivolts is used. It will be apparent to one skilled in the art that other mediator and electrode material combinations will require different test voltages. The duration of first test voltage $V_1$ is generally from about 0.1 and 1.0 seconds and is typically about 0.5 seconds. Typically, time S is measured relative to time $t_1$. In practice, the current values $I_i$ are the average of a set of measurements obtained over a short interval, for example, 5 measurements obtained at 0.01 second intervals starting at about 0.5 seconds. The person of ordinary skill in the art will recognize that other intervals may also be used.

Referring to FIG. 7, a first rest voltage $V_{R1}$ of about −50 to about +50 millivolts, typically zero millivolts, is applied between first working electrode 12 and reference electrode 10. The duration of rest voltage $V_{R1}$ is generally from about 0.05 to about 1.0 second. More typically the duration of the voltage is about 0.1 seconds.

In the subject method, a second test voltage $V_2$ is applied between first working electrode 12 and reference electrode 10 at time $t_2$ and a second current value $I_2$ is measured at or near the end of second test voltage $V_2$ at time $S_2$. Second test voltage $V_2$ applied between first working electrode 12 and reference electrode 10 is generally from about +100 millivolts to about +600 millivolts or from about negative 100 millivolts to about negative 600 millivolts. In one embodiment in which first working electrode 12 is a carbon ink and the mediator is ferricyanide, a test voltage of about +400 millivolts is used. In another embodiment in which first working electrode 12 is a carbon ink and the mediator is ruthenium hexamine trichloride, a test voltage of about +200 millivolts is used. It will be apparent to one skilled in the art that other mediator and electrode material combinations will require different test voltages. The duration of second test voltage $V_2$ is generally from about 0.1 and 1.0 seconds and is typically about 0.5 seconds. Typically, time $S_2$ is measured relative to time $t_2$. In exemplary embodiments, test voltages $V_1$ and $V_2$ used to obtain first and second current values $I_1$ and $I_2$ have the same magnitude and duration.

In the subject method, a second rest voltage $V_{R2}$ of about −50 to about +50 millivolts, typically zero millivolts, is applied between first working electrode 12 and reference electrode 10. The duration of rest voltage $V_{R2}$ is generally from about 0.05 to about 1.0 second. More typically the duration of the voltage is about 0.1 seconds. In exemplary embodiments, rest voltages $V_{R1}$ and $V_{R2}$ have the same magnitude and duration.

In the subject method, a third test voltage $V_3$ is applied between first working electrode 12 and reference electrode 10 at time $t_3$ and a third current value $I_3$ is measured at or near the end of third test voltage $V_3$ at time $S_3$. Third test voltage $V_3$ applied between first working electrode 12 and reference electrode 10 is generally from about +100 millivolts to about +600 millivolts or from about negative 100 millivolts to about negative 600 millivolts. In one embodiment in which first working electrode 12 is a carbon ink and the mediator is ferricyanide, a test voltage of about +400 millivolts is used. In another embodiment in which first working electrode 12 is a carbon ink and the mediator is ruthenium hexamine trichloride, a test voltage of about +200 millivolts is used. It will be apparent to one skilled in the art that other mediator and electrode material combinations will require different test voltages. The duration of third test voltage $V_3$ is generally from about 0.1 and 1.0 seconds and is typically about 0.5 seconds. Typically, time $S_3$ is measured relative to time $t_3$. In exemplary embodiments, test voltages $V_1$, $V_2$ and $V_3$ used to obtain first, second and third current values $I_1$, $I_2$ and $I_3$ have the same magnitude and duration.

The above steps may be repeated once or several times as desired to obtain a third or more current values $I_i$. Illustratively, three test voltages $V_1$, $V_2$ and $V_3$ with corresponding current values $I_1$, $I_2$ and $I_3$, measured at $S_1$, $S_2$ and $S_3$ are shown in FIGS. 9 and 10 but four or more test voltages could also be used. In exemplary embodiments, five test voltages are used. Typically, times $S_i$ are measured relative to time $t_i$. In an exemplary embodiment, all the test voltages $V_i$ are the same both in terms of magnitude and duration. Likewise, all rest voltage $V_{Ri}$ are typically the same both in terms of magnitude and duration.

In the subject method, the substantially hematocrit-independent analyte concentration in the sample is calculated from the first, second and third current values. Methods of calculating the substantially hematocrit-independent glucose concentration of samples according to this step are illustrated in relation to FIG. 9 and Examples 1 and 2 which will be described below.

FIG. 9 illustrates a typical logarithmic plot of current value as a function of the time at which the current value is measured. Using standard regression techniques, a straight line L1 on the logarithmic plot is obtained. A corrected current value $I_0$ at time $t_1$ (corresponding to S equals zero seconds or $S_0$) can be calculated from line L1. Corrected current value $I_0$ corresponds to a hematocrit-corrected value of current value $I_1$. If the sample is a whole blood sample, then $I_0$ is generally insensitive to the hematocrit fraction of the sample and is therefore substantially hematocrit independent.

Example 1

The Method According to the Present Invention is Used to Determine the Substantially Hematocrit Independent Glucose Concentration in Whole Blood Samples The data are obtained with test strips from the same manufacturing batch to avoid batch-to-batch variability. For the purposes of the tests, whole blood samples are used. The blood samples are used within 30 hours of collection, with lithium heparin as the anti-coagulant. Each blood sample is divided into aliquots and adjusted as required with glucose to give samples with glucose concentrations in the range of 50 to 650 milligram per deciliter (mg/dl) glucose. The glucose concentration of each aliquot is determined using a YSI 2300 STAT Plus Glucose & Lactate Analyzer (available from YSI Life Sciences, Yellow Springs, Ohio). The hematocrit fraction h of each aliquot is also determined using standard centrifugal techniques and is measured as the fraction of red blood cells present in a whole blood sample. Hematocrit fractions are adjusted as required by the addition of red blood cells or blood plasma to the samples to obtain samples with a hematocrit range from 0.20 to 0.70.

Figure 11:
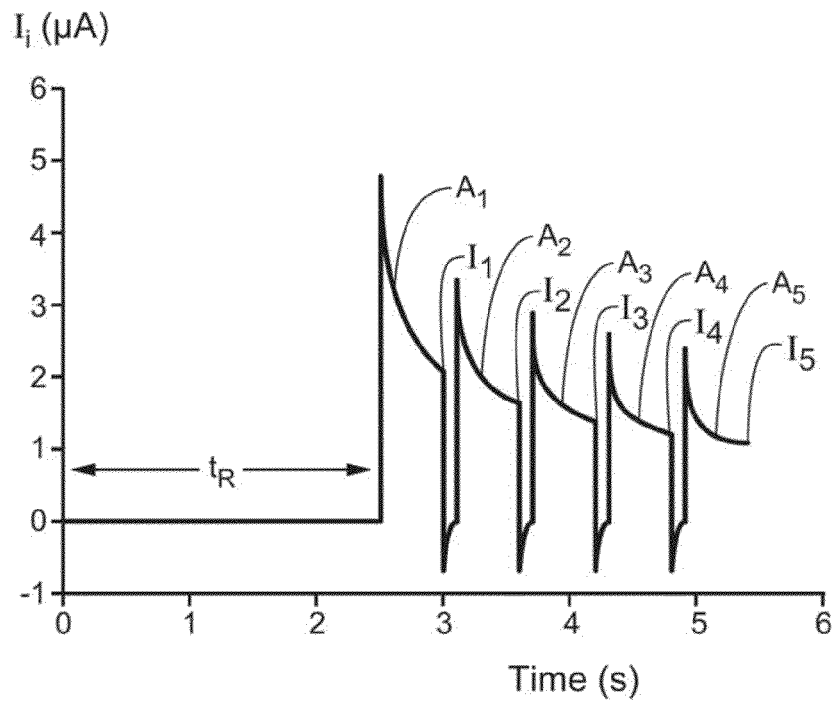
FIG. 11 is a graphical representation of the current transients obtained when the five test voltages of FIG. 10 are applied to a test strip according to a method.
Figure 12:
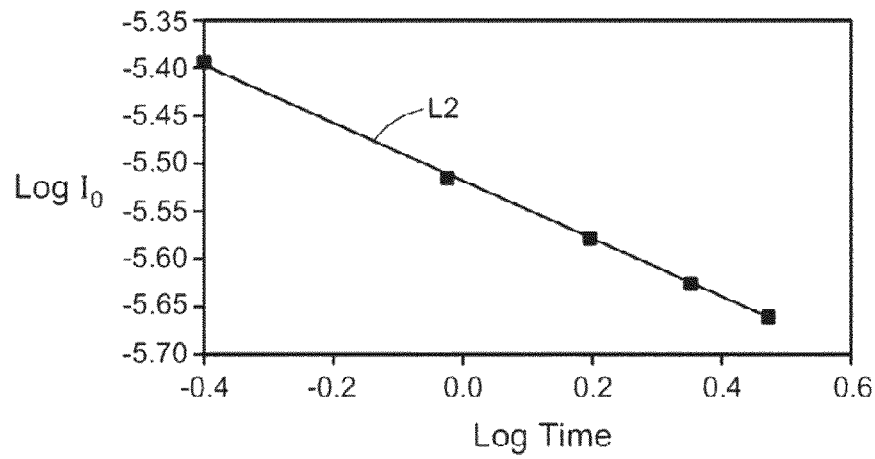
FIG. 12 is a logarithmic graph of the current values $I_1$ to $I_5$ obtained from the current transients shown in FIG. 13 plotted as a function of the time at which the current values are measured according to a method.
Figure 13:
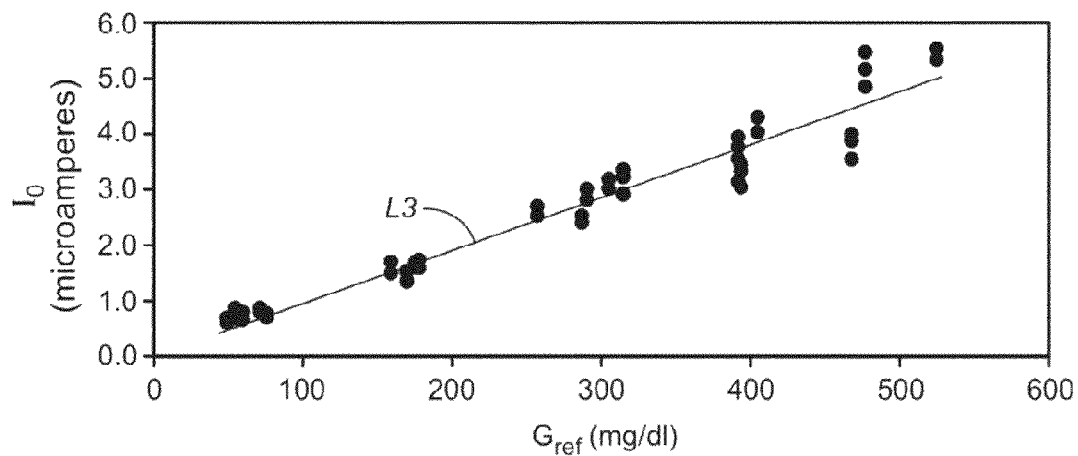
FIG. 13 is a plot of experimental data showing the relationship between current value $I_0$ obtained with samples of varying glucose and hematocrit concentration and the glucose concentration obtained on a reference instrument according to a method.
Figure 14:
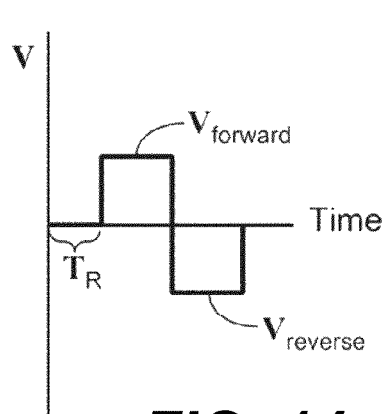
FIG. 14 is a graphical representation of a constant test voltage applied to a second working electrode of a test strip according to a method.
Figure 15:
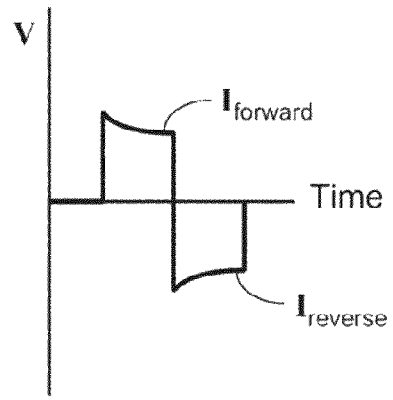
FIG. 15 is a graphical representation of a current transient obtained when the constant test voltage of FIG. 14 is applied to a test strip according to a method.

A laboratory meter is connected to one working electrode and the reference electrode of a sensor of the OneTouch Ultra test strip type. An example of method in which a plurality of test voltages is applied to the test strip and the measured current transients resulting from the plurality of test voltages are depicted in FIGS. 12 and 13 respectively. A test voltage (not shown in FIG. 10) of 400 millivolts is initially applied between reference and first working electrodes 10, 12. An aliquot of whole blood having a known glucose and hematocrit concentration is then applied to the test strip. The presence of sufficient quantity in the reaction zone of the test strip is determined by measuring the current flowing through first working electrode 12. The beginning of reaction period $t_R$ is determined to begin when the current flowing through first working electrode 12 reaches a sufficient level, typically about 0.150 nanoamperes (not shown in FIG. 10), at which time a rest voltage $V_R$ of zero millivolts is applied between first working electrode 12 and reference electrode 10. After a reaction period $t_R$ of 2.5 seconds during which time reagent layer 22 is allowed to react with the sample, a timer in the laboratory meter causes first test voltage $V_1$ of 400 millivolts to be applied between first working electrode 12 and reference electrode 10. Contemporaneously, current transient $A_1$ is measured at first working electrode 12 (see FIG. 11). Test voltage $V_1$ is applied for a period of 0.5 seconds at the end of which time first current value $I_1$ is measured. At the end of test voltage $V_1$, rest voltage $V_R$ of zero millivolts is applied between first working electrode 12 and reference electrode 10 for a duration of 0.1 seconds. After 0.1 seconds, a second test voltage $V_2$ of 400 millivolts is applied for 0.5 seconds to obtain a second current value $I_2$. The procedure is repeated to obtain three further current values $I_3$, $I_4$ and $I_5$, corresponding to voltages $V_3$, $V_4$ and $V_5$, respectively.

Referring again to FIG. 11, current values $I_1$ to $I_5$ are obtained from the set of current transients $A_1$ to $A_5$. The time t at which each value of $I_1$ to $I_5$ is obtained is measured relative to the initiation of first test voltage $V_1$. The current values $I_1$ to $I_5$ are usually calculated from current transients $A_1$ to $A_5$ immediately prior to the removal of voltages $V_1$ to $V_5$. FIG. 12 is a plot of the base-10 logarithm of time at which current value is measure on the x-axis against the base-10 logarithm of the corresponding current values $I_1$ to $I_5$ on the y-axis. Using standard data regression techniques, a line L2 is obtained having slope $m_1$ and intercept $c_1$ (not shown). Corrected current value $I_0$, which represents a hematocrit-corrected value of $I_1$, is obtained by using Equation 4 below.

$$\log(I_0) = m_1 * \log(t) + c_1 \quad (4)$$

Where:
t is the time at which each current value $I_i$ is measured;
log(t) is the base-10 logarithm of t; and
log($I_0$) is the base-10 logarithm of corrected current value $I_0$.

Corrected current value $I_0$ is determined for each sample tested and the plot shown in FIG. 13 is then obtained. The y-axis is corrected current value $I_0$ in amperes. The x-axis is the glucose concentration $G_{ref}$ in mg/dL of the aliquots taken from the same whole blood samples as above are measured on a reference glucose analyzer (i.e., the YSI 2300 STAT Plus Glucose & Lactate Analyzer). A line L3 is obtained using standard linear regression techniques. The slope of line L3 is used to calculate a corrected blood glucose concentration $G_0$ in mg/dL from corrected current values $I_0$ according to Equation 5 below.

$$G_0 = \frac{(I_0 - c_2)}{m_2} \quad (5)$$

Where:

$G_0$ is the blood glucose concentration of the aliquot corresponding to corrected current value $I_0$ and is therefore a substantially hematocrit independent blood glucose concentration;

$c_2$ is the intercept value obtained from the straight line of FIG. 13 by linear regression; and $m_2$ is the slope of the line shown in FIG. 13.

The method is also useful for discriminating between a whole blood sample and a control solution that is used to test for proper functioning of the meter. Such control solutions are described, for example in U.S. Pat. Nos. 5,187,100 and 5,605,837. Generally the slope of line L1 (as shown in FIG. 9) measured using a control solution aliquot is different from the slope of line L1 measured using a whole blood aliquot with a hematocrit fraction between 0.20 and 0.70. Hence by determining slope $m_1$ of line L1 by using Equation 6 below, it is possible to determine whether an aliquot of whole blood or an aliquot of control solution is present on the test strip.

$$m_1 = \frac{\log(I_0) - c_1}{\log(t)} \quad (6)$$

In practice, an acceptance range for the slope of line L1 for whole blood and control solution is stored in the metering system and if the slope of line L1 falls outside the acceptance range for either type of sample, an error message is displayed on the metering system.

Figure 16:
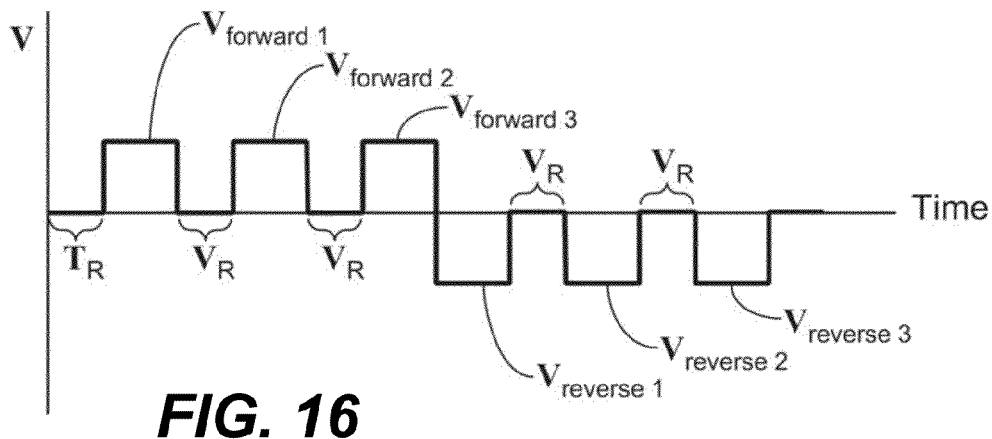
FIG. 16 is a graphical representation of a forward test voltage and a reverse test voltage applied to a test strip according to a method.
Figure 17:
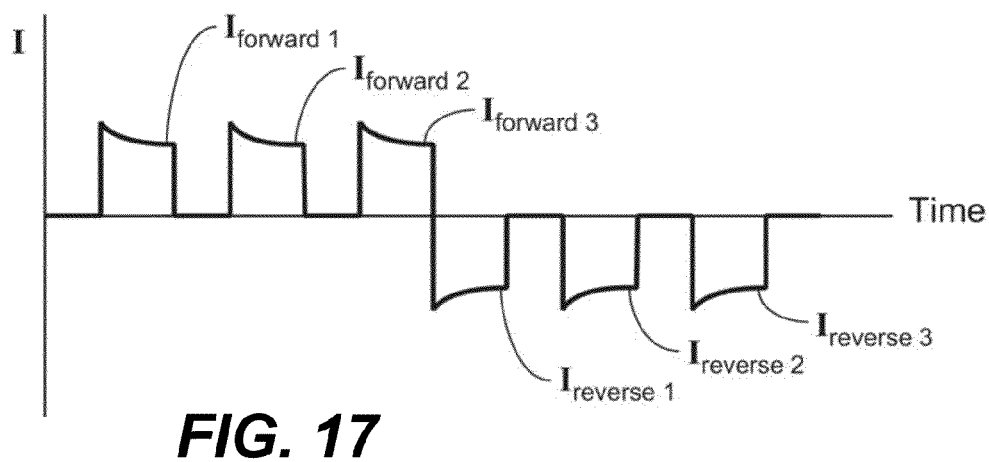
FIG. 17 is a graphical representation of the current transients obtained when the forward and reverse test voltages of FIG. 17 are applied to a test strip according to a method.

Another embodiment includes a method of determining the presence of sufficient fluid sample in a test strip. In one embodiment shown in FIGS. 16 and 17, after applying a forward test voltage $V_{forward}$ to test strip 90 and measuring a forward current value $I_{forward}$ near the end of forward test voltage $V_{forward}$, reverse test voltage $V_{reverse}$ is applied between first working electrode 12 and reference electrode 10 and a reverse current value $I_{reverse}$ is measured near the end of $V_{reverse}$. Forward test voltage $V_{forward}$ applied between first working electrode 12 and reference electrode 10 is generally from about +100 millivolts to about +600 millivolts. In one embodiment in which first working electrode 12 is a carbon ink and the mediator is ferricyanide, a forward test voltage of about +400 millivolts is used. In another embodiment in which first working electrode 12 is a carbon ink and the mediator is ruthenium hexamine trichloride, a forward test voltage of about +200 millivolts is used. Reverse test voltage $V_{reverse}$ applied between first working electrode 12 and reference electrode 10 is generally from about −100 millivolts to about −600 millivolts. In one embodiment in which first working electrode 12 is a carbon ink and the mediator is ferricyanide, a reverse test voltage of about −400 millivolts is used. In another embodiment in which first working electrode 12 is a carbon ink and the mediator is ruthenium hexamine trichloride, a reverse test voltage of about −200 millivolts is used. The duration of forward and reverse test voltages is generally from about 0.1 to about 1.0 second or, more typically, is about 0.5 seconds. The measured reverse current value $I_{reverse}$ can be used for diagnostic and quantitative purposes to determine, for example, whether sufficient quantity is present on the strip to conduct the test by calculating the ratio of the absolute value of reverse current value $I_{reverse}$ to forward current value $I_{forward}$. In many cases, such current ratio $I_{reverse}/I_{forward}$ lies within an expected range, typically about 2:1 for a test strip in which the reference electrode is approximately twice the surface area of the working electrode, and is generally indicative of the proper functioning of the test strip. In practice, an acceptance range for the current ratio $I_{reverse}/I_{forward}$ is stored in the metering system and if the current ratio $I_{reverse}/I_{forward}$ falls outside the acceptance range, an error message is displayed on the metering system.

Figure 18:
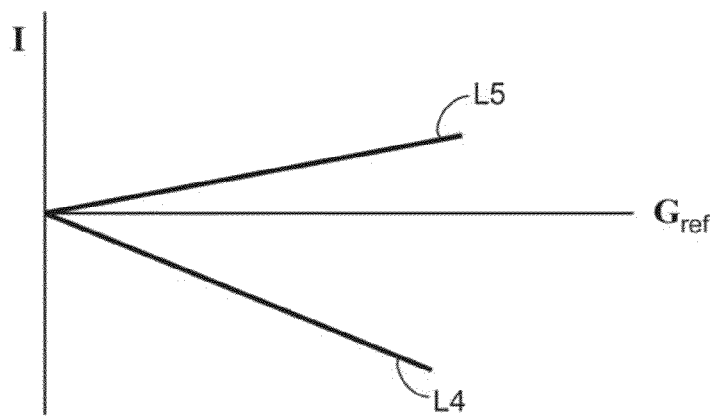
FIG. 18 is a graphical representation of a plurality of forward and reverse test voltages applied to a test strip according to a method.

In yet another embodiment in which the presence of sufficient quantity is determined, calculation step (h) of the subject method is preceded or followed by an additional step in which a plurality of reverse test voltages $V_{reverse}$ of opposite polarity and substantially equal magnitude to the first, second and third test voltages applied between first working 12 and reference electrode 10. In the embodiment shown in FIGS. 18 and 19, the first, second and third test voltages of the subject method are defined as the first, second and third forward test voltages $V_{forward1}$, $V_{forward2}$ and $V_{forward3}$. After applying the plurality of forward test voltages $V_{forward1}$, $V_{forward2}$ and $V_{forward3}$ between working electrode 12 and reference electrode 10, a plurality of reverse test voltages $V_{reverse1}$, $V_{reverse2}$ and $V_{reverse3}$ is applied to test sensor 90. Each of the forward and reverse test voltages are separated by about 0.05 to about 1.0 seconds (typically about 0.1 seconds) at which time a rest voltage $V_R$ of about −50 to about +50 millivolts, and more typically zero millivolts, is applied between the working and reference electrodes. Each of the forward test voltages applied between first working electrode 12 and reference electrode 10 is generally from about +100 millivolts to about +600 millivolts. In one embodiment in which first working electrode 12 is a carbon ink and the mediator is ferricyanide, each of the forward test voltages is about +400 millivolts. In another embodiment in which first working electrode 12 is a carbon ink and the mediator is ruthenium hexamine trichloride, each of the forward test voltages is about +200 millivolts. Each of the reverse test voltages applied between first working electrode 12 and reference electrode 10 is generally from about −100 millivolts to about −600 millivolts. In one embodiment in which first working electrode 12 is a carbon ink and the mediator is ferricyanide, each of the reverse test voltages is about −400 millivolts. In another embodiment in which first working electrode 12 is a carbon ink and the mediator is ruthenium hexamine trichloride, each of the reverse test voltages is about −200 millivolts. At the end of each of the forward test voltages applied to the test strip (e.g., after about 0.1 to about 1.0 seconds or, more typically, about 0.5 seconds for each forward test voltage), a forward current value $I_{forward1}$, $I_{forward2}$, and $I_{forward3}$ is measured. Similarly, at the end of each of the reverse test voltages applied to the test strip (e.g., after about 0.1 to about 1.0 seconds or, more typically, about 0.5 seconds for each reverse test voltage), a reverse current value $I_{reverse1}$, $I_{reverse2}$, and $I_{reverse3}$ is measured. Referring to FIG. 18, a slope $m_{reverse}$ is then calculated from a linearly regressed line L4 obtained from the reverse current values plotted as a function of glucose concentration of the test sample as measured with a reference instrument. A slope $m_{forward}$ is also calculated for a linearly regressed line L5 generated from the forward values plotted as a function of glucose concentration of the test sample as measured with a reference instrument. The absolute value of the slope ratio $m_{reverse}/m_{forward}$ is then calculated to determine whether sufficient quantity is present on the test strip to conduct the test. In many cases, such slope ratios lie within an expected range, typically about 2:1 for a test strip in which the reference electrode is twice the surface area of the working electrode, and are generally indicative of the proper functioning of the strip. In practice, an acceptance range for the slope ratio $m_{reverse}/m_{forward}$ is stored in the metering system and if the slope ratio $m_{reverse}/m_{forward}$ falls outside the acceptance range, an error message is displayed on the metering system.

While not wishing to be bound by any particular theory, it is believed that the application of a negative pulse reduces the measurement error resulting from the presence of electrochemically active species such as ascorbic acid. Further methods for obtaining useful diagnostic and quantitative information when a current value is obtained by applying a constant voltage of opposite polarity are shown and described in U.S. Pat. No. 6,475,372, which is hereby incorporated by reference in its entirety into this application.

Figure 19:
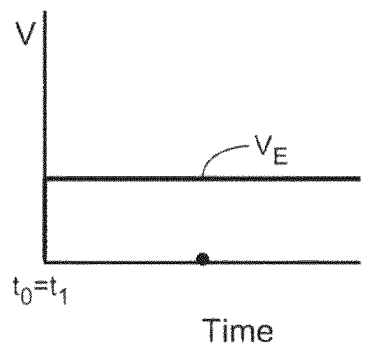
FIG. 19 is a graphical representation of the current transients obtained when the plurality of forward and reverse test voltages of FIG. 19 are applied to a test strip according to a method.
Figure 20:
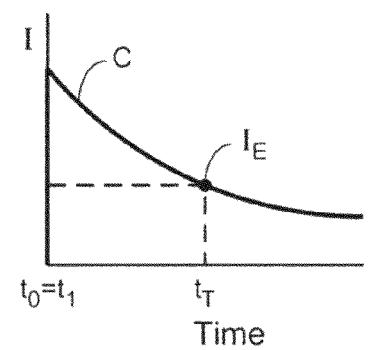
FIG. 20 is a graphical representation of the forward and reverse current values obtained from the current transients shown in FIG. 20 plotted as a function of glucose concentration of the test sample as measured on a reference instrument.

Another embodiment includes a method of determining the hematocrit-dependent concentration of an analyte and the hematocrit concentration in a whole blood sample in the calculation step is preceded or followed by an additional step in which a constant test voltage $V_E$ is applied to second working electrode 14 and the reference electrode 10, as described in Example 2 and shown in FIG. 19. The presence of sufficient quantity is detected in a similar manner to the previously described embodiments. Constant test voltage $V_E$ is then applied between second working electrode 14 and reference electrode 10 at a level from about 100 millivolts to about 600 millivolts, generating a current transient C (see FIG. 20). Constant test voltage $V_E$ applied between second working electrode 14 and reference electrode 10 may be applied at the same time as a plurality of test voltages $V_i$ is applied to first working electrode 12. Constant test voltage $V_E$ may also be applied between second working electrode 14 and reference electrode 10 either before or after the plurality of test voltages $V_i$ are applied to first working electrode 12. In one embodiment shown in FIG. 19, constant test voltage $V_E$ is applied to test strip 90 prior to the plurality of test voltages $V_i$; thus, $t_0$ equals $t_1$. After test voltage $V_E$ is applied to the test strip (e.g., after about 1 to about 5 seconds or, more typically, about 5 seconds), a current value $I_E$ is measured at the second working electrode (see FIG. 20). Current value $I_E$ is then used to calculate the hematocrit-dependent analyte concentration. To calculate the hematocrit-dependent analyte concentration, a curve similar to that shown in FIG. 13 is generated by testing fluid samples (e.g., whole blood) containing various analyte and hematocrit concentrations and plotting current value as a function of the analyte concentration (e.g., glucose) as determined on a reference instrument. When a fluid sample of unknown analyte concentration is tested, current value $I_E$ is determined as described above and the analyte concentration is read off of the calibration curve stored in the metering system.

Generally current value $I_E$ can be approximately represented by the following equation:

$$I_E = \left(\frac{1-kh}{1-kh_0}\right)(m_3 G + c_3) \quad (7)$$

Where:

h is the hematocrit fraction based on the fraction of red blood cells in the whole blood sample;

$h_0$ is the hematocrit value for a normal patient whole blood sample (e.g., 0.42);

G is the blood glucose concentration of the whole blood sample measured in milligram per deciliter (mg/dl); and k, $m_3$ and $c_3$ are parameters derived by standard regression techniques from the experimental data.

Equation 7 shows that current value $I_E$ is dependent upon both the hematocrit fraction and the glucose concentration of the sample.

Similarly, Equation 5 can be solved for the substantially hematocrit-independent current value $I_0$ to obtain the following equation:

$$I_0 = m_2 G_0 + c_2 \quad (8)$$

where $G_0$, $m_2$ and $c_2$ are as described previously.

Since $I_0$ is generally not sensitive to the hematocrit fraction, Equation 8 generally contains no term for the hematocrit fraction.

Equation 7 and Equation 8 can be rearranged and simplified to obtain the following equation which represents the hematocrit fraction h of the sample as a function of the current values $I_E$ and $I_0$:

$$h = K^I + \frac{(h_0 - K^I)I_E}{(K^{II} I_0 + K^{III})} \quad (11)$$

Where:

$$K^I = \frac{1}{k}; \quad (12)$$

$$K^{II} = \frac{m_3}{m_2}; \quad (13)$$

$$K^{III} = c_3 - c_2\left(\frac{m_3}{m_2}\right); \quad (14)$$

$I_E$ is the current value measured near the end of the time period at which a constant test voltage is applied to the second working electrode; and $I_0$ is the hematocrit-corrected value of current value $I_1$ measured near the end of the time period at which first test voltage $V_1$ is applied to the first working electrode.

Thus, Equation 11 may be used to calculate the hematocrit fraction h from current values obtained simultaneously at both working electrodes.

In yet another embodiment, calculation step (h) of the subject method is preceded or followed by an error checking step in which the functionality of the test strip is determined. Such an error checking step determines if, for example, the test strip has been damaged, the test strip is past its expiration date, an incorrect voltage has been applied to the test strip, the voltage has been applied to the test strip at an incorrect time, and/or the test strip has not filled completely with the fluid sample. The error checking step may also eliminate the need for a control solution to determine if the metering system is functioning properly.

Figure 21:
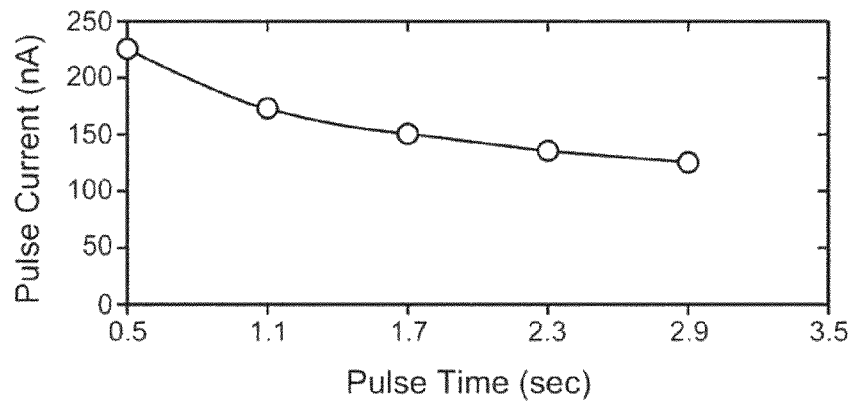
FIG. 21 is a plot of current value as a function of pulse time $t_i$, in which time is measured relative to initiation of a first test voltage and five test voltages are applied to the test strip such that i varies from 1 to 5 according to a method.

In the error checking step, five current values $I_1$ to $I_5$ are graphed as a function of pulse time in which the time is measured relative to initiation of the first test voltage (see FIG. 21). The metering system uses least squares regression to fit the data in FIG. 21 to equation 15 below.

$$I_i = \alpha\sqrt{\frac{t_i}{t_1}} + \beta\left(1 - \frac{t_i}{t_1}\right) + \eta_i \qquad (15)$$

Where:

$I_i$ is the current value measured at or near the end of each test voltage (e.g., current values $I_1$ to $I_5$ described above) obtained at pulse time $t_i$ in which i varies from 1 to 5; and $\eta_i$ is a noise term.

The values for $\alpha$ and $\beta$ are initially unknown; thus, the metering system calculates estimated values, $\hat{\alpha}$ and $\hat{\beta}$, respectively, by using the equations below.

$\hat{\alpha}$ is a first shape parameter defined by the following equation:

$$\hat{\alpha} = \sum_{i=1}^{n} \lambda_i I_i \qquad (16)$$

Where:

$I_i$ is the current value measured at or near the end of each test voltage (e.g., current values $I_1$ to $I_5$ described above) obtained at pulse time $t_i$ in which i varies from 1 to 5;

$$\lambda_i = \frac{S_{XX}Y_i - S_{XY}X_i}{\Delta}; \qquad (17)$$

$$X_i = 1 - \frac{t_i}{t_1}; \qquad (18)$$

$$Y_i = \sqrt{\frac{t_i}{t_1}}; \qquad (19)$$

$$S_{AB} = \sum_{i=1}^{n} A_i B_i; \qquad (20)$$

$$\Delta = S_{XX}S_{YY} - S_{XY}^2; \qquad (21)$$

$\hat{\beta}$ is a second shape parameter defined by the following equation:

$$\hat{\beta} = \sum_{i=1}^{n} \theta_i I_i \qquad (22)$$

Where:

$$\theta_i = \frac{S_{YY}X_i - S_{XY}Y_i}{\Delta}; \qquad (23)$$

$$X_i = 1 - \frac{t_i}{t_1}; \qquad (24)$$

$$Y_i = \sqrt{\frac{t_i}{t_1}}; \qquad (25)$$

$$S_{AB} = \sum_{i=1}^{n} A_i B_i; \text{ and} \qquad (26)$$

$$\Delta = S_{XX}S_{YY} - S_{XY}^2. \qquad (27)$$

$\lambda$ and $\hat{\theta}$ values are calculated for each of the five pulse times $t_1$ through $t_5$ using equations 17 and 23, respectively, and these $\lambda$ and $\theta$ values are stored in a look up table in the metering system. After the calculation step based on the first through third current values in the subject method, the five current values $I_1$ to $I_5$ are substituted into equations 16 and 22 along with $\lambda$ and $\theta$ values, respectively, that are chosen from the look up table to generate $\hat{\alpha}$ and $\hat{\beta}$ values that result in a best fit to the current value versus pulse time data. A $$\frac{\hat{\alpha}}{\hat{\beta}}$$

ratio is then calculated to error check the test strip and is compared to a range of $$\frac{\hat{\alpha}}{\hat{\beta}}$$

ratios for a test strip with a normal response that is stored in the metering system. If the calculated $$\frac{\hat{\alpha}}{\hat{\beta}}$$

ratio is not within the acceptable range for normal responses (e.g., the $$\frac{\hat{\alpha}}{\hat{\beta}}$$

ratio is from about 4 to about 14), the metering system displays an appropriate error message. A look up table for $\lambda$ and $\theta$ values is used in the metering system to reduce the amount of memory required. In another embodiment, the pulse times $t_i$ (instead of $\lambda$ and $\theta$ values) are stored in a look up table in the metering system and least squares regression is again used to calculate $\hat{\alpha}$ and $\hat{\beta}$ values.

Figure 22:
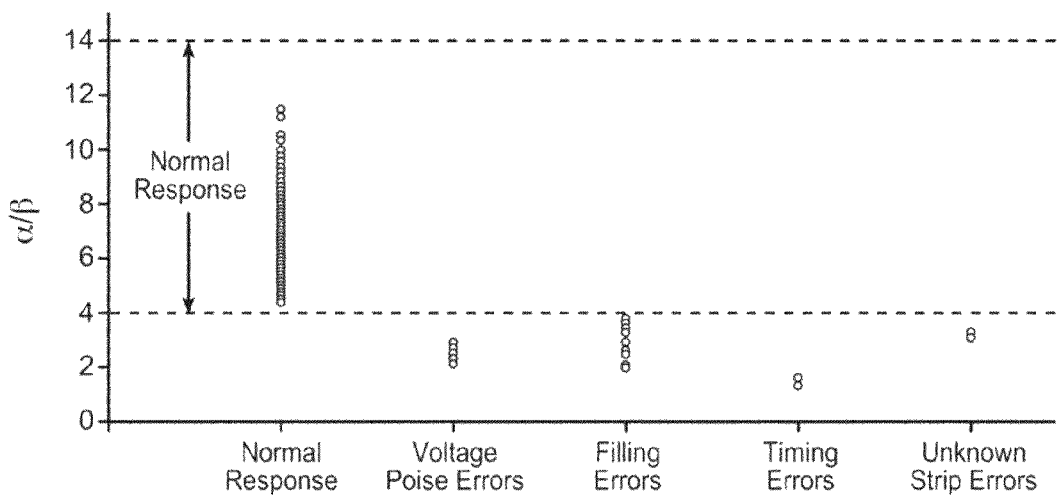
FIG. 22 is a graph illustrating $$\frac{\hat{\alpha}}{\hat{\beta}}$$

FIG. 22 illustrates $$\frac{\hat{\alpha}}{\hat{\beta}}$$

ratios for test strips exhibiting a normal response and with strips exhibiting various errors including voltage poise errors (e.g., incorrect test voltage applied to the test strip), strip filling errors, timing errors (e.g., test voltage applied at the wrong time) and errors due to unknown causes. The data show that the $$\frac{\hat{\alpha}}{\hat{\beta}}$$

ratios can be used to distinguish between strips with normal responses and strips exhibiting various errors. As with the previous embodiment, if the calculated ratio is not within an acceptable range for normal responses (e.g., the $\frac{\hat{\alpha}}{\hat{\beta}}$ ratio is from about 4 to about 14), the metering system displays an appropriate error message.

In yet another embodiment, $\frac{\hat{\alpha}}{\hat{\beta}}$ ratios are used to distinguish between non-aged test strips and aged test strips that are past their expiration date or have been exposed to deleterious conditions and if used, might give inaccurate or invalid test results. In FIG. 23, frequency of occurrence of each $\frac{\hat{\alpha}}{\hat{\beta}}$ value as a percentage of total $\frac{\hat{\alpha}}{\hat{\beta}}$ values determined is plotted as a function of $\frac{\hat{\alpha}}{\hat{\beta}}$ ratio in the form of a bar diagram for non-aged test strips (e.g., group B) and test strips that were placed at 50° C. for six weeks (e.g., group A). The data show that the $\frac{\hat{\alpha}}{\hat{\beta}}$ ratio for aged and non-aged test strips is different. In FIG. 23, for example, the $\frac{\hat{\alpha}}{\hat{\beta}}$ ratio is for non-aged test strips is from about 4 to about 14 and the $\frac{\hat{\alpha}}{\hat{\beta}}$ ratio is less than about 4 for aged test strips. Thus, $\frac{\hat{\alpha}}{\hat{\beta}}$ ratio may be used to determine if the test strip is past the expiration date or if the test strip has been exposed to deleterious conditions. In practice, an acceptance range for the $\frac{\hat{\alpha}}{\hat{\beta}}$ ratio would be stored in the metering system and if the $\frac{\hat{\alpha}}{\hat{\beta}}$ ratio for a test strip were outside the acceptance range, an appropriate error message would be displayed on the metering system.

In another exemplary embodiment, $\frac{\hat{\alpha}}{\hat{\beta}}$ ratios may be used to distinguish control solution from whole blood. Current values obtained after each test voltage are different for whole blood and control solution, resulting in different $\hat{\alpha}$ and $\hat{\beta}$ values calculated with equations 15 and 21 for each type of sample. Thus the $\frac{\hat{\alpha}}{\hat{\beta}}$ ratio will be unique for each type of sample. In practice, an acceptance range for the $\frac{\hat{\alpha}}{\hat{\beta}}$ ratio would be stored in the metering system for control and whole blood samples and if the $\frac{\hat{\alpha}}{\hat{\beta}}$ ratio for a test strip were outside the acceptance range for either type of sample, an appropriate error message would be displayed on the metering system. As a non-limiting example, the $$\frac{\hat{\alpha}}{\hat{\beta}}$$

ratio for a whole blood sample may be from about 4 to about 14 and the $$\frac{\hat{\alpha}}{\hat{\beta}}$$

ratio for a control solution may be greater than about 14.

In an alternative embodiment of this invention, a test strip 300 may be used that has a first working electrode 306 in the form of a microelectrode array 310 as shown in FIG. 25. In general, microelectrode array 310 will enhance the effects of radial diffusion causing an increase in the measured current density (current per unit area of the working electrode). As a result of the enhanced radial diffusion, the application of a limiting test voltage to microelectrode array 310 can cause a test current to achieve a non-zero steady-state value that is independent of time. In contrast, the application of a limiting test voltage to a non-microelectrode will result in a test current that approaches zero as time progresses. Because the steady-state value is independent of time for a microelectrode array 310, an effective diffusion coefficient of the mediator in the blood sample may be calculated. In turn, the effective diffusion coefficient can be used as an input into an algorithm for reducing the effects of hematocrit.

FIG. 25 illustrates a distal portion 302 of a test strip 300 that is partially assembled. The conductive layer is visible through aperture 18 in insulation layer 16. The conductive layer is coated on substrate 5 and includes a first working electrode 306, a second working electrode 308, and a reference electrode 304. First working electrode 306 is in the form of a microelectrode array 310 that includes a plurality of microelectrodes 320.

Another embodiment of a test strip 400 having a microelectrode array is shown in FIG. 26. Test strip 400 differs from test strip 300 in that test strip 400 has a first working electrode 406 located upstream of a reference electrode 404 and a fill detect electrode 412. First working electrode 406 is in the form of a microelectrode array 410 that includes a plurality of microelectrodes 420. In an alternative geometry for test strip 400, working electrode 406 may be downstream from reference electrode 404.

FIG. 27 is a cross-sectional view through microelectrode array 310 on first working electrode 306 of FIG. 25 showing that an insulation portion 330 is disposed on first working electrode 306. Thus, in this embodiment, insulation portion 330 is printed in the same step as the printing of insulation layer 16. Laser ablating insulation portion 330 to expose a plurality of disk shaped microelectrode 320 may then form microelectrode array 310.

In another embodiment, insulation portion 330 is disposed on first working electrode 306 in a step separate from the printing of insulation layer 16. Insulation portion 330 may be disposed over and bound to first working electrode 306 by processes such as ultrasonic welding, screen-printing, or through the use of an adhesive. In this embodiment, the holes in insulation portion 330 may be formed before or after adhering insulation portion 330 to first working electrode 306.

FIGS. 31 and 32 are cross-sectional views through microelectrode array 310 on first working electrode 306 of FIG. 25 with additional layers including reagent layer 22, adhesive pads 24 and 26, and hydrophilic portion 32. Reagent layer 22 may be disposed on distal hydrophilic portion 32 as shown in FIG. 25. Alternatively, reagent layer 22 may be disposed over insulation portion 330 as shown in FIG. 26.

In order for microelectrode array 310 to have an enhanced effect due to radial diffusion, insulation portion 330 should have the appropriate dimensions. In one aspect, insulation portion 330 may have a height H that is about 5 microns or less. It is necessary that insulation portion 330 be sufficiently thin so as to allow radial diffusion. If insulation portion 330 were much greater than 5 microns, then insulation portion 330 would interfere with radial diffusion and would actually promote planar diffusion.

In another aspect, each microelectrode 320 should be spaced sufficiently far from each other so as to prevent a first microelectrode from competing with an adjacent second microelectrode for oxidizing mediator. Each microelectrode 320 may be spaced apart with a distance B ranging from about 5 times to about 10 times the diameter of microelectrode 320. In one embodiment as shown in FIG. 27, each microelectrode 320 may be evenly spaced throughout insulation portion 330, where a microelectrode may have six neighboring microelectrodes which form a hexagonal shape In yet another aspect, each microelectrode 320 should be sufficiently small such that the proportion of the test current ascribed to radial diffusion is greater than the proportion of the test current ascribed to planar diffusion. Microelectrode 320 may be in the form of a circle having a diameter A ranging from about 3 microns to about 20 microns.

In an alternative embodiment of this invention, a test strip may be used that employs a process of laser ablation for improving the accuracy and precision of the measured analyte concentration. The process of laser ablation on a conductive layer allows the edge definition of the electrode area to be better controlled than with other processes such as screen-printing. For example, the resolution of screen-printing may be limited by the size of the openings in the screen for printing a reagent layer. When using screen-printing to define the electrode pattern, an edge of the conductive layer may be jagged because of the granularity caused by the plurality of openings in the screen. In addition, as will be later described, a laser ablated pattern in the conductive layer may be used to substantially define the electrode area without the need of an insulation layer or an adhesive layer.

FIG. 24 illustrates a top exploded perspective view of an unassembled test strip 500, which may be used with the proposed algorithms. Test strip 500 includes a conductive layer 501, a reagent layer 570, and a top tape 81. Test strip 500 also includes a distal portion 576, a proximal portion 578, and two sides 574. Top layer 80 includes a clear portion 36 and an opaque portion 38. Thus, test strip 500 has the advantage of eliminating the step of printing an insulation layer for substantially defining the electroactive area for a first working electrode 546, a second working electrode 548, and a reference electrode 544.

It should be understood that various alternatives to the embodiments of the invention described herein may be employed in practicing the invention. It is intended that the following claims define the scope of the invention and that structures and methods within the scope of these claims and their equivalents be covered thereby.

What is claimed is:

1. A method of detecting the presence of sufficient quantity of a fluid sample deposited on a test strip having a reference electrode and a working electrode, in which the working electrode is coated with a reagent layer, the method comprising:

applying a forward test voltage between the reference electrode and the working electrode and measuring a forward current value near the end of the forward test voltage, in which the forward test voltage is from about 100 millivolts to about 600 millivolts;

applying a reverse test voltage of opposite polarity and substantially equal magnitude to the forward test voltage between the reference electrode and the working electrode and measuring a reverse current value near the end of the reverse test voltage, the reverse test voltage being from about negative 100 millivolts to about negative 600 millivolts;

calculating a ratio of the reverse current value to the forward current value; and determining if the ratio of the reverse current value to the forward current value is within an acceptance range, the acceptance range being substantially equal to two when the reference electrode is about twice the surface area of the working electrode; and detecting the presence of sufficient quantity of the fluid sample based on the ratio.

2. The method of claim 1, in which the duration of the forward test voltage ranges from about 0.1 to about 1.0 seconds; the magnitude of the forward test voltage is about 400 millivolts;

the forward current value is measured at about 0.1 to about 1.0 seconds after the forward test voltage is applied to the test strip; the duration of the reverse test voltage ranges from about 0.1 to about 1.0 seconds; the magnitude of the reverse test voltage is about 400 millivolts; and the reverse current value is measured at about 0.1 to about 1.0 seconds after the reverse test voltage is applied to the test strip.

3. The method of claim 2, in which the working electrode comprises a plurality of microelectrodes formed from gold.

4. The method of claim 2, in which the reagent layer comprises an enzyme, a mediator and a buffering solution in which the mediator is ruthenium hexamine chloride ranging in amount from about 15 percent to about 20 percent based on a ratio of a weight of the mediator to a volume of the buffering solution.

5. The method of claim 1, further comprising:

wherein applying the forward test voltage comprises applying a first forward test voltage between the reference electrode and the working electrode and measuring a first forward current value near the end of the first forward test voltage, applying a second forward test voltage between the reference electrode and the working electrode and measuring a second forward current value near the end of the second forward test voltage and applying a third forward test voltage between the reference electrode and the working electrode and measuring a third forward current value near the end of the third forward test voltage;

wherein applying the reverse test voltage comprises applying a first reverse test voltage between the reference electrode and the working electrode and measuring a first reverse current value near the end of the first reverse test voltage, applying a second reverse test voltage between the reference electrode and the working electrode and measuring a second reverse current value near the end of the second reverse test voltage and applying a third reverse test voltage between the reference electrode and the working electrode and measuring a third reverse current value near the end of the third reverse test voltage;

plotting the first, second and third reverse current values as a function of an analyte concentration as measured on a reference instrument and calculating a slope $m_{reverse}$ of the linear regressed line obtained therefrom;

plotting the first, second and third forward current values as a function of the analyte concentration as measured on a reference instrument and calculating a slope $m_{forward}$ of the linear regressed line obtained therefrom;

calculating a ratio of $m_{reverse}$ to $m_{forward}$; and determining if the ratio of $m_{reverse}$ to $m_{forward}$ is within an acceptance range, the acceptance range being substantially equal to two when the reference electrode is about twice the surface area of the working electrode, the first, second and third forward test voltages and first, second and third reverse test voltages are of equal magnitude and duration.

6. The method of claim 5, in which the duration of the forward test voltage ranges from about 0.1 to about 1.0 seconds; the magnitude of the forward test voltage is about 400 millivolts;

the forward current value is measured at about 0.1 to about 1.0 seconds after the forward test voltage is applied to the test strip; the duration of the reverse test voltage ranges from about 0.1 to about 1.0 seconds; the magnitude of the reverse test voltage is about 400 millivolts; and the reverse current value is measured at about 0.1 to about 1.0 seconds after the reverse test voltage is applied to the test strip.

7. The method of claim 6, in which the reagent layer comprises an enzyme, a mediator and a buffering solution in which the mediator is ruthenium hexamine chloride ranging in amount from about 15 percent to about 20 percent based on a ratio of a weight of the mediator to a volume of the buffering solution.

* * * * *